United States Patent
Chawla

(10) Patent No.: US 11,096,983 B2
(45) Date of Patent: *Aug. 24, 2021

(54) ANGIOTENSIN II ALONE OR IN COMBINATION FOR THE TREATMENT OF HYPOTENSION

(71) Applicant: The George Washington University a Congressionally Chartered Not-for-Profit Corporation, Washington, DC (US)

(72) Inventor: Lakhmir S. Chawla, McLean, VA (US)

(73) Assignee: The George Washington University a Congressionally Chartered Not-for-Profit Corporation, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/382,850

(22) Filed: Apr. 12, 2019

(65) Prior Publication Data

US 2019/0328827 A1 Oct. 31, 2019

Related U.S. Application Data

(63) Continuation of application No. 16/135,608, filed on Sep. 19, 2018, now Pat. No. 10,765,722, which is a continuation of application No. 15/909,617, filed on Mar. 1, 2018, now Pat. No. 10,493,124, which is a continuation of application No. 14/941,301, filed on Nov. 13, 2015, now Pat. No. 10,028,995, which is a continuation of application No. 14/575,127, filed on Dec. 18, 2014, now Pat. No. 9,220,745.

(60) Provisional application No. 61/955,706, filed on Mar. 19, 2014, provisional application No. 61/917,576, filed on Dec. 18, 2013.

(51) Int. Cl.
| | |
|---|---|
| *A61K 38/08* | (2019.01) |
| *A61K 31/137* | (2006.01) |
| *A61K 9/00* | (2006.01) |
| *A61P 9/02* | (2006.01) |
| *A61K 31/135* | (2006.01) |

(52) U.S. Cl.
CPC .......... *A61K 38/085* (2013.01); *A61K 9/0019* (2013.01); *A61K 31/135* (2013.01); *A61K 31/137* (2013.01); *A61P 9/02* (2018.01)

(58) Field of Classification Search
None
See application file for complete search history.

(56) References Cited

U.S. PATENT DOCUMENTS

| | | | |
|---|---|---|---|
| 4,330,532 A | 5/1982 | Nyeki et al. | |
| 5,216,025 A | 6/1993 | Gross et al. | |
| 5,444,067 A | 8/1995 | Kivlighn et al. | |
| 6,592,865 B2 | 7/2003 | Parry et al. | |
| 7,666,408 B2 | 2/2010 | Bachmann | |
| 9,220,745 B2 | 12/2015 | Chawla | |
| 9,457,059 B2 | 10/2016 | Tidmarsh | |
| 9,572,856 B2 | 2/2017 | Chawla | |
| 9,867,863 B2 | 1/2018 | Chawla | |
| 10,028,995 B2 | 7/2018 | Chawla | |
| 10,322,160 B2 | 6/2019 | Chawla | |
| 10,335,451 B2 | 7/2019 | Chawla | |
| 2010/0172862 A1 | 7/2010 | Correia et al. | |
| 2011/0144026 A1* | 6/2011 | Chawla | ..................... A61P 9/00 514/15.6 |
| 2016/0074465 A1 | 3/2016 | Tidmarsh | |
| 2016/0129072 A1 | 5/2016 | Chawla | |
| 2017/0014471 A1 | 1/2017 | Tidmarsh | |
| 2017/0095526 A1 | 4/2017 | Chawla | |
| 2017/0196931 A1 | 7/2017 | Chawla | |
| 2017/0224761 A1 | 8/2017 | Tidmarsh et al. | |
| 2018/0133282 A1 | 5/2018 | Chawla | |
| 2018/0311306 A1 | 11/2018 | Tidmarsh et al. | |

FOREIGN PATENT DOCUMENTS

| | | |
|---|---|---|
| WO | WO 2007/146900 A2 | 12/2007 |
| WO | WO 2008/059062 A1 | 5/2008 |
| WO | WO 2012/009545 A1 | 1/2012 |
| WO | WO 2014/176534 A1 | 10/2014 |
| WO | 2015/095535 A1 | 6/2015 |

(Continued)

OTHER PUBLICATIONS

Salerno et al., "Diagnosis, Prevention and Treatment of Hepatorenal Syndrome in Cirrhosis," Recent Advanced in Clinical Practice GUT , 2007; 56: 1310-1318. [Cited in parent U.S. Appl. No. 14/941,301, filed Nov. 13, 2015].
Sansoe et al., "Inappropriately low angiotensin II generation: a factor determining reduced kidney function and survival in patient with decompensated cirrhosis," 2004; 40: 417-423. [Cited in parent U.S. Appl. No. 14/941,301, filed Nov. 13, 2015].
Schroeder et al., "Renal Failure in Patients with Cirrhosis of the Liver," Am J Med, 1967; 43(6): 887-96. [Cited in parent U.S. Appl. No. 14/941,301, filed Nov. 13, 2015].
Simon et al., "Duration and magnitude of hypotension and monocyte deactivation in patients with community-acquired pneumonia," Shock, 36(6), pp. 553-559 (Dec. 2011). [Cited in parent U.S. Appl. No. 14/941,301, filed Nov. 13, 2015].

(Continued)

*Primary Examiner* — Christina Bradley
(74) *Attorney, Agent, or Firm* — Sterne, Kessler, Goldstein & Fox P.L.L.C.

(57) ABSTRACT

The present invention relates, inter alia, to a method comprising administering to a subject having high output shock and undergoing treatment with a catecholamine at a dose equivalent to at least about 0.2 mcg/kg/min of norepinephrine a dose of angiotensin II which is effective to raise the blood pressure of the subject to a mean arterial pressure (MAP) of about 6.5 mm Hg or above, and which is effective to reduce the dose of the catecholamine required to maintain a MAP of about 65 mm Hg to the equivalent of about 0.05-0.2 mcg/kg/min norepinephrine or less, or to the equivalent of about 0.05 mcg/kg/min norepinephrine or less.

27 Claims, 4 Drawing Sheets
Specification includes a Sequence Listing.

(56) References Cited

FOREIGN PATENT DOCUMENTS

| | | |
|---|---|---|
| WO | WO 2016/007589 A1 | 1/2016 |
| WO | WO 2017/120438 A1 | 7/2017 |
| WO | WO 2017/120440 A1 | 7/2017 |
| WO | WO 2018/191678 A1 | 10/2018 |

OTHER PUBLICATIONS

Struthers et al., Review of aldosterone- and angiotensin II-induced target organ damage and prevention. Cardiovasc Res 2004, 61(4):663-670. [Cited in parent U.S. Appl. No. 14/941,301, filed Nov. 13, 2015].

Thomas, V.L. et al., "Administration of Angiotensin II in refractory septic shock," Critical Care Medicine, vol. 19, No. 8, pp. 1084-1086, 1991. [Cited in parent U.S. Appl. No. 14/941,301, filed Nov. 13, 2015].

Tremblay et al., "Effect of Hypotension Preceding Death on the Function of Lungs from Donors with Nonbeating Hearts," The Journal of Heart and Lung Transplantation, vol. 15, No. 3, pp. 260-268 (1996). [Cited in parent U.S. Appl. No. 14/941,301, filed Nov. 13, 2015].

Trilli et al., Lisinopril overdose and management with intravenous angiotensin II. Ann Pharmacother 1994, 28 (10):1165-1168. [Cited in parent U.S. Appl. No. 14/941,301, filed Nov. 13, 2015].

Uchino et al., Acute renal failure in critically ill patients: a multinational, multicenter study. JAMA 294:813-818, 2005. [Cited in parent U.S. Appl. No. 14/941,301, filed Nov. 13, 2015].

Unknown Author, "NSC1076711," http://www.repository.cam.ac.uk/handle/1810/88629 (Jun. 21, 2017). [Cited in parent U.S. Appl. No. 14/941,301, filed Nov. 13, 2015].

Valle, J.C. et al., "Angiotensin II modulates cardiovascular autonomic control in the absence of baroreflex loading," Heart, vol. 80, pp. 127-133, 1998. [Cited in parent U.S. Appl. No. 14/941,301, filed Nov. 13, 2015].

Vincent et al., The SOFA (Sepsis-related Organ Failure Assessment) score to describe organ dysfunction/failure. On behalf of the Working Group on Sepsis-Related Problems of the European Society of Intensive Care Medicine. Intensive Care Med 1996, 22(7):707-710. [Cited in parent U.S. Appl. No. 14/941,301, filed Nov. 13, 2015].

Vincent JL, De Backer D: Circulatory shock. N Engl J Med 2013, 369(18):1726-1734. [Cited in parent U.S. Appl. No. 14/941,301, filed Nov. 13, 2015].

Walpole et al., BMC Public Health, 2012, 12:439. [Cited in parent U.S. Appl. No. 14/941,301, filed Nov. 13, 2015].

Wan, L. et al., "Angiotensin II in experimental hyperdynamic sepsis," Critical Care vol. 13, No. 6, pp. 1-10, 2009. [Cited in parent U.S. Appl. No. 14/941,301, filed Nov. 13, 2015].

Weisgerber et al., "Vasopressin analogue injection as ultimate measure for counteracting severe catecholamine-refractory poisoning by several vasodilators taken with suicidal intent," Dtsch Med Wochenschr, pp. 2189-5192 (2003). [Cited in parent U.S. Appl. No. 14/941,301, filed Nov. 13, 2015].

Whiteley et al., Treatment of hypotension in septic shock. Lancet 1996, 347(9001):622. [Cited in parent U.S. Appl. No. 14/941,301, filed Nov. 13, 2015].

Wilson et al., U.S. trends in CABG hospital volume: the effect of adding cardiac surgery programs. Health Aff 26:162-168, 2007. [Cited in parent U.S. Appl. No. 14/941,301, filed Nov. 13, 2015].

Wray, G.M. et al., "Severe septic shock unresponsive to nonadrenaline," Lancet vol. 346, p. 1604, 1995. [Cited in parent U.S. Appl. No. 14/941,301, filed Nov. 13, 2015].

Yunge M. et al., "Angiotensin for septic shock unresponsive to noradrenaline," Arch Dis Child 2000, Vo. 82, pp. 388-389, 2014. [Cited in parent U.S. Appl. No. 14/941,301, filed Nov. 13, 2015].

Ziegler et al., "Hepatorenal Syndrome: A Disease Mediated by the Intrarenal Action of Renin," Med Hypothesis, 1976; 2: 15-213. [Cited in parent U.S. Appl. No. 14/941,301, filed Nov. 13, 2015].

Griffin et al., "Angiotensin II Causes Vascular Hypertrophy in Part by a Non-pressor Mechanism," Hypertension, 17 (5):626-635 (1991).

Sigma-Aldrich Co., Production information, Angiotensin II, human, Apr. 13, 2012. [Cited in parent U.S. Appl. No. 14/941,301, filed Nov. 13, 2015].

Xue et al., "Sensitization of Slow Pressor Angiotensin II (ANGII) Initiated Hypertension: Induction of Sensitization by Prior ANGII Treatment," Hypertension, 59(2): pp. 459-466 (Feb. 2012). [Cited in parent U.S. Appl. No. 14/941,301, filed Nov. 13, 2015].

Ames et al., "Prolonged Infusions of Angiotensin II and Norepinephrine and Blood Pressure, Electrolyte Balance, and Aldosterone and Cortisol Secretion in Normal Man and in Cirrhosis and Ascites," Journal of Clinical Investigation, 1965; 44(7): 1171-1186. [Cited in parent U.S. Appl. No. 14/941,301, filed Nov. 13, 2015.].

Angus et al., Epidemiology of severe sepsis in the United States: Analysis of incidence, outcome, and associated costs of care. Crit Care Med 29:1303-1310, 2001. [Cited in parent U.S. Appl. No. 14/941,301, filed Nov. 13, 2015.].

Avanzini et al., Journal of Hypertension, 2006, vol. 24, No. 12, 2377-2385. [Cited in parent U.S. Appl. No. 14/941,301, filed Nov. 13, 2015.].

Bacgenm, "Angiotensin II acetate salt," http://shop.bachem.com/h-1705.html (Mar. 31, 2017). [Cited in parent U.S. Appl. No. 14/941,301, filed Nov. 13, 2015.].

Bagshaw et al., A Multi-Centre Evaluation of the Rifle Criteria for Early Acute Kidney Injury in Critically Ill Patients. Nephrol Dial Transplant Oct. 25 (Epub): 2007. [Cited in parent U.S. Appl. No. 14/941,301, filed Nov. 13, 2015.].

Basso et al., History about the discovery of the renin-angiotensin system. Hypertension 2001, 38(6):1246-1249. [Cited in parent U.S. Appl. No. 14/941,301, filed Nov. 13, 2015.].

Busse et al., P160 "Angiotensin II may be used for the treatment of hypotension in distributive shock, but a safe and efficacious dose is unknown", Critical Care 2014, vol. 18, Supp11, http://ccforum.com/supplements/18/51, p. S57. [Cited in parent U.S. Appl. No. 14/941,301, filed Nov. 13, 2015.].

Campbell, D.J., "Do intravenous and subcutaneous angiotensin II increase blood pressure by different mechanisms?," Frontiers in Research Review: Evolving Concepts of the Renin-Angiotensin System, Clinical and Experimental Pharmacology and Physiology, 40, 560-570, 2013. [Cited in parent U.S. Appl. No. 14/941,301, filed Nov. 13, 2015.].

Chawla, L.S. et al., "Intravenous Angiotensin II for the Treatment of Hihg-output Shock (ATHOS trial): A Pilot Study," Critical Care, vol. 18, Issue 5, Article No. 534, published on-line Oct. 6, 2014. [Cited in parent U.S. Appl. No. 14/941,301, filed Nov. 13, 2015.].

Cohn, J., et al., "Studies in Clinical Shock and Hypotension. II. Hemodynamic Effects of Norepinephrine and Angiotensin," Journal of Clinical Investigation, vol. 44, No. 9, pp. 1494-1504, 1965. [Cited in parent U.S. Appl. No. 14/941,301, filed Nov. 13, 2015.].

Corrëa, T.D. MD, et al., "Angiotensin II in Septic Shock: Effects on Tissue Perfusion, Organ Function, and Mitochondrial Respiration in a Porcine Model of Fecal Peritonitis," Clinical Care Mediine, vol. 42, No. 8, pp. e550-e559, 2014. [Cited in parent U.S. Appl. No. 14/941,301, filed Nov. 13, 2015.].

Daskalopoulos et al., "Effects of captopril on renal function in patients with cirrhosis and ascites," Journal of Hepatology, 1987; 4: 330-336. [Cited in parent U.S. Appl. No. 14/941,301, filed Nov. 13, 2015.].

Del Greco, F.D. MD, et al., "Clinical Experience with Angiotensin II in the Treatment of Shock," J.A.M.A., vol. 178, No. 10, pp. 130-135, 1961. [Cited in parent U.S. Appl. No. 14/941,301, filed Nov. 13, 2015.].

Dellinger, R.P. et al., "Surviving Sepsis Campaign: International Guidelines for Management of Severe Sepsis and Septic Shock: 2012," Critical Care Medicine, vol. 41, No. 2, pp. 580-657, 2013. [Cited in parent U.S. Appl. No. 14/941,301, filed Nov. 13, 2015.].

Downing, S.E., "Effects of Angiotensin II and Norepinephrine on Ventricular Performance During Oligemic Shock," The Yale Journal of Biology and Medicine, Inc., vol. 36, pp. 407-420, 1964. [Cited in parent U.S. Appl. No. 14/941,301, filed Nov. 13, 2015.].

Dworkin, Br. J. Cancer 71, 942-944, 1995. [Cited in parent U.S. Appl. No. 14/941,301, filed Nov. 13, 2015.].

(56) References Cited

OTHER PUBLICATIONS

Eriksson et al., "Just the Beginning: Novel Functions for Angiotensin-Converting Enzymes," Current Biology, Vo. 12, R745-752 (Oct. 29, 2012). [Cited in parent U.S. Appl. No. 14/941,301, filed Nov. 13, 2015.].
Gines et al., "Hepatorenal syndrome," Lancet, 362(9398): 1819-1827 (2003). [Cited in parent U.S. Appl. No. 14/941,301, filed Nov. 13, 2015.].
Goldsmith et al., Effect of a pressor infusion of angiotensin II on sympathetic activity and heart rate in normal humans. Circ Res 1991, 68(1):263-268. [Cited in parent U.S. Appl. No. 14/941,301, filed Nov. 13, 2015.].
Harrison-Bernard, L.M., The renal renin-angiotensin system. Adv Physiol Educ, (2009) 33(4): p. 270-74. [Cited in parent U.S. Appl. No. 14/941,301, filed Nov. 13, 2015.].
Helmy et al., "Nitric oxide mediates the reduced vasoconstrictor response to angiotensin II in patients with preascitic cirrhosis," Journal of Hepatology, 2003; 38: 44-50. [Cited in parent U.S. Appl. No. 14/941,301, filed Nov. 13, 2015.].
Heringlake et al., Renal dysfunction according to the ADQI-RIFLE system and clinical practice patterns after cardiac surgery in Germany. Minerva Anestesiol 72:645-654, 2006. [Cited in parent U.S. Appl. No. 14/941,301, filed Nov. 13, 2015.].
Jackson et al., Enalapril overdose treated with angiotensin infusion. Lancet 1993, 341(8846):703. [Cited in parent U.S. Appl. No. 14/941,301, filed Nov. 13, 2015.].
Kakavas et al., "Vasoactive support in the optimization of post-cardiac arrest hemodynamic status: From pharmacology to clinical practice," European Journal of Pharmacology 667 (2011), pp. 34-40. [Cited in parent U.S. Appl. No. 14/941,301, filed Nov. 13, 2015.].
Kanaparthi et al., Distributive Shock, Medscape Reference, Feb. 13, 2013. [Cited in parent U.S. Appl. No. 14/941,301, filed Nov. 13, 2015.].
Kopacova et al., "Hepatorenal syndrome," World Journal of Gastroenterology, 2012; 18(36): 4978-4984. [Cited in U.S. Appl. No. 14/941,301, filed Nov. 13, 2015.].
Kuitunen et al., Acute renal failure after cardiac surgery: evaluation of the RIFLE classification. Ann Thorac Surg 81:542-546, 2006. [Cited in parent U.S. Appl. No. 14/941,301, filed Nov. 13, 2015.].
LaGrange et al., Hypertension, 2003; 42:1124-1129. [Cited in parent U.S. Appl. No. 14/941,301, filed Nov. 13, 2015.].
Laragh et al., "Angiotensin II, Norepinephrine, and Renal Transport of Electrolytes and Water in Normal Man and in Cirrhosis with Ascites," Journal of Clinical Investigation, 1963; 42(7): 1179-1192. [Cited in parent U.S. Appl. No. 14/941,301, filed Nov. 13, 2015.].
Lata et al., "Hepatorenal syndrome," World Journal of Gatroenterology, 2012, 18936: 4978-4984. [Cited in parent U.S. Appl. No. 14/941,301, filed Nov. 13, 2015.].
Le et al., "Angiotensin IV is a Potent Agonist for Contitutive Active Human AT1 Receptors," The Journal of Biological Chemistry, Vo. 277, No. 26, pp. 23107-23110 (2002). [Cited in parent U.S. Appl. No. 14/941,301, filed Nov. 13, 2015.].
Lee et al., "34-Year-Old Woman With Hypotension, Respiratory Failure, Fever, and an Abdominal Mass," West J Med, 158: 499-505 (1993). [Cited in parent U.S. Appl. No. 14/941,301, filed Nov. 13, 2015.].
Li, T. et al., "Changes in Sensitivity of Vascular Smooth Muscle to Calcium and Its Role in the Biphasic Change in Vascular Reactivity Following Hemorrhagic Shock in Rats," Chinese Critical Care Medicine, vol. 17, No. 11, pp. 647-650, Nov. 2005, English Abstract only. [Cited in parent U.S. Appl. No. 14/941,301, filed Nov. 13, 2015.].
Lianos et al., "Angiotensin-induced sodium excretion patterns in cirrhosis: Role of renal prostaglandins," Kidney International, 1982; 21: 70-77. [Cited in parent U.S. Appl. No. 14/941,301, filed Nov. 13, 2015.].
Lopes et al., Prognostic utility of RIFLE for acute renal failure in patients with sepsis. Crit Care 11:408, 2007. [Cited in parent U.S. Appl. No. 14/941,301, filed Nov. 13, 2015.].

Mayo Clinic, Septis Symptoms—Mayo Clinic, accessed on Jun. 12, 2015, available online at: http://www.mayoclinic.org/diseases-conditions/sepsis/basics/syrnptoms/con-20031900. [Cited in parent U.S. Appl. No. 14/941,301, filed Nov. 13, 2015.].
McCloy et al., "Angiotensis-induced Natriuresis in Cirrhosis in the Absence of Endogenous Aldosterone Secretion," Ann Intern Med, 1966; 64(6): 1271-1276. [Cited in parent U.S. Appl. No. 14/941,301, filed Nov. 13, 2015.].
Morelli et al., Singer M: Effect of heart rale control with esmolol on hemodynamic and clinical outcomes in patients with septic shock: a randomized clinical trial. JAMA 2013, 310(16):1683-1691. [Cited in parent U.S. Appl. No. 14/941,301, filed Nov. 13, 2015.].
Morrell et al., "The Management of Severe Sepsis and Septic Shock," Infect. Dis. Clin. N. Am. 23 (2009) pp. 485-501. [Cited in parent U.S. Appl. No. 14/941,301, filed Nov. 13, 2015.].
Myburgh et al., CAT Study investigators: A comparison of epinephrine and norepinephrine in critically ill patients. Intensive Care Med 2008, 34(12):2226-2234. [Cited in parent U.S. Appl. No. 14/941,301, filed Nov. 13, 2015.].
Nassif, A.C. et al., "Angiotensin II in Treatment of Hypotensive States," J.A.M.A. vol. 183, No. 9, pp. 751-754, 1963. [Cited in parent U.S. Appl. No. 14/941,301, filed Nov. 13, 2015.].
Newby D.E. et al., "Enalapril overdose and the corrective effect of intravenous angiotensin II," Br. J. Clin Pharmacol, vol. 40, pp. 103-104, 1995. [Cited in parent U.S. Appl. No. 14/941,301, filed Nov. 13, 2015.].
Newby et al., "Peripheral vascular tone in patients with cirrhosis: role of the renin-angiotensin and sympathetic nervous systems," Cardiovascular Research, 1998; 38: 221-228. [Cited in parent U.S. Appl. No. 14/941,301, filed Nov. 13, 2015.].
Niu, C.Y. et al., "Lymphatic Hyporeactivity and Calcium Desensitization Following Hemorrhagic Shock," Shock, vol. 37, No. 4, pp. 415-423, Apr. 2012. [Cited in parent U.S. Appl. No. 14/941,301, filed Nov. 13, 2015.].
O'Brien et al., "Terlipressin for norepinephrine-resistant septic shock," Research Letters, The Lancelet, vol. 359, pp. 1209-1210 (2002). [Cited in parent U.S. Appl. No. 14/941,301, filed Nov. 13, 2015.].
Page, I.H. et al., "Angiotensin," Physiological , vol. 41, pp. 331-390, 1961. [Cited in parent U.S. Appl. No. 14/941,301, filed Nov. 13, 2015.].
Rona G: Catecholamine cardiotoxicity. J Mol Cell Cardiol 1985, 17(4):291-306. [Cited in parent U.S. Appl. No. 14/941,301, filed Nov. 13, 2015.].
Rose, J. MD, et al., "Comprison of Effects of Angiotensin and Norepinephrine on Pulmonary Circulation, Systemic Arteries and Veins, and Systemic Vascular Capacity in the Dog," Circulation, vol. 25, pp. 247-252, 1962. [Cited in parent U.S. Appl. No. 14/941,301, filed Nov. 13, 2015.].
Russell et al., VASST Investigators: Vasopressin versus norepinephrine infusion in patients with septic shock. N Engl J Med 2008, 358(9):877-887. [Cited in parent U.S. Appl. No. 14/941,301, filed Nov. 13, 2015.].
Ryding, J. et al., "Reversal of 'Refractory Septic Shock' vby Infusion of Amrinone and Angiotensin II in an Anthracycline-Treated Patient," Chest, 107, 201-203, 1995. [Cited in parent U.S. Appl. No. 14/941,301, filed Nov. 13, 2015.].
Vittorio, T., et al., "Vasopressor Response to Angiotensin II Infusion in Patients With Chronic Heart Failure Receiving β-Blockers," Circulation 107:290-293, American Heart Associate, United States (2003).
Workeneh, B., et al., "Acute Kidney Injury Treatment & Management," Medscape (2017), https://emedicine.medscape.com/article/243492-treatment, accessed on May 14, 2018.
Rahman, M., et al., "Acute Kidney Injury: A Guide to Diagnosis and Management," American Family Physician 86(7): 631-639, American Academy of Family Physicians, United States (2012).
Lankadeva, Y., et al., "Urinary Oxygenation as a Surrogate Measure of Medullary Oxygenation During Angiotensin II Therapy in Septic Acute Kidney Injury," Critical Care Medicine 46(1): e41-e48, Society of Critical Care Medicine and Wolters Kluwer Health, Inc. (2018).

(56) References Cited

OTHER PUBLICATIONS

Non-Final Office Action dated Jul. 24, 2018, for U.S. Appl. No. 15/870,139, filed Jan. 12, 2018.
Non-Final Office Action dated May 18, 2018, for U.S. Appl. No. 15/922,513, filed Mar. 15, 2018.
"Intravenous AII for the Treatment of Severe Hypotension in High Output Shock: A Pilot Study," NCT01393782, Mar. 14, 2013, 3 pages.
"Diagnosis and treatment for acute circulatory failure, Catecholamines' Focus on Presentation and Case Presentation," Therapeutic Research, 25(9): 1763-1773, Life Science Publishing (2004).
Al-Merani, et al., "The Half-Lives of Angiotensin II, Angiotensin II-Amide, Angiotensin III, Sar$^1$-ALA$^8$-Angiotensin II and Renin in the Circulatory System of the Rat," J Physiol, 278: 471-490, Wiley-Blackwell, Great Britain (1978).
Bradley, S., et al., "The Hemodynamic Effects of Angiotonin in Normal Man," J Clin Invest, 20(6): 715-719, American Society for Clinical Investigation, United States (1941).
Chawla et al., "The Use of Angiotensin II in Distributive Shock," Critical Care, 20(1):137, BioMed Central, United States, (2016).
Collier, J.G., et al., "Comparison of Effects of Locally Infused Angiotensin I and II on Hand Veins and Forearm Arteries in Man: Evidence for Converting Enzyme Activity in Limb Vessels," Clin Sci Mol Med, 47(2):189-192 Biochemical Society, United Kingdom (1974).
Conti, C., et al., "Modulation of Vascular Reactivity after Acute Calcium Antagonist Administration in Pregnant Women Moderately Sensitive to Angiotensin Infusion," J. Biol. Res., 70(10-11):243-248 PubMed Journal, United States (1994).
Cziraki, A. et al., "Quantification of Pulmonary Capillary Endothelium-bound Angiotensin Converting Enzyme Inhibition in Man," Gen Pharmacol, 35(4): 213-218, Elsevier, Netherlands (2002).
De Pasquale, N., et al., "Effect of angiotensin II on the intact Forearm Veins of Man," Circ Res, 13:239-245, American Heart Association, United States (1963).
Derrick, J., et al., "Adjunctive Use of a Biologic Pressor Agent, Angiotensin, in Management of Shock," Circulation, 25: 263-267, American Heart Association, United States (1962).
Eadington, D.W., et al., "Urinary dopamine response to angiotensin II is not abnormal in type 1 (insulin-dependent) diabetes mellitus," Nephrol Dial Transplant, 8(1):36-40 Oxford University Press, United Kingdom (1993).
Egner, B., et al., "Noninvasive Blood Pressure Monitoring: A Review," NAVC Clinician's Brief, 71-74 United States (2010).
Extended European Search Report for EP Application No. 18158219.8, dated Jun. 28, 2018.
Extended European Search Report for EP Application No. 15775357.5, dated Apr. 22, 2016.
Finnerty, F., et al., "Evaluation of the Pressor, Cardiac, and Renal Hemodynamic Properties of Angiotensin II in Man," Circ Res, 9:256-263 American Heart Association, United States (1961).
Fyhrquist, F., et al., "Renin-angiotensin system revisited," Journal of Internal Medicine, 264: 224-236 Wiley-Blackwell, Great Britain (2008).
Goldsmith, S., et al., "Angiotensin II and Sympathetic Activity in Patients With Congestive Heart Failure," JACC, 15(5): 1107-1113 Elsevier, Netherlands (1993).
Hou, Y., et al., "Ferulic acid inhibits vascular smooth muscle cell proliferation induced by angiotensin II," Eur J Pharmacol, 499(1-2): 85-90 Elsevier, Netherlands (2004).
Hou, J., et al., "Angiotensin II-induced Cardiac Fibrosis in the Rat is Increased by Chronic Inhibition of Nitric Oxide Synthase," J Clin Invest, 96: 2469-2477 American Society for Clinical Investigation, United States (1995).
International Search Report and Written Opinion for International Application No. PCT/US2017/012485, Israel Patent Office, Israel, dated Apr. 27, 2017, 12 pages.
International Search Report and Written Opinion for International Application No. PCT/US2017/012487, Israel Patent Office, Israel, dated Apr. 27, 2017, 14 pages.
International Search Report and Written Opinion for International Application No. PCT/US2018/027593, Israel Patent Office, Israel, dated Jul. 22, 2018, 16 pages.
International Search Report and Written Opinion for PCT/US2014/035511, Australian Patent Office, Australia, dated Jul. 1, 2014, 8 pages.
Jones, A., et al., "The Sequential Organ Failure Assessment score for predicting outcome in patients with severe sepsis and evidence of hypoperfusion at the time of emergency department presentation," Crit. Care Med., 37(5): 1649-1654, Society of Critical Care Medicine and Lippincott Williams & Wilkins (2009).
Kanaide, H., et al., "Cellular Mechanism of Vasoconstriction Induced by Angiotensin II It Remains to be Determined," Circ Res, 93: 1015-1017, American Heart Association, United States (2003).
Kienbaum et al., "Alterations in Forearm Vascular Reactivity in Patients with Septic Shock," Anaesthesia, 63: 121-128, The Association of Anaesthetists of Great Britain and Ireland, United Kingdom (2008).
Kürer et al., "Hepatorenal Syndrome," Der Anaesthesist 55(1): 95-109 Springer, Berlin, De, Germany (2006).
Landry, D., et al., "Vasopressin Pressor Hypersensitivity in Vasodilatory Septic Shock," Crit Care Med, 25(8): 1279-1282 Lippincott Williams & Wilkins, United States (1997).
Lottermoser, K., et al., "Differential Effect of Acute Angiotensin II Type 1 Receptor Blockade on the Vascular and Adrenal Response to Exogenous Angiotensin II in Humans," American Journal of Hypertension, 16: 445-452 Oxford University Press, United Kingdom (2003).
Millar, E., et al., "Activity of the renin-angiotensin system in acute severe asthma and the effect of angiotensin II on lung function," Thorax, 49(5):492-495 BMJ Group, United Kingdom (1994).
Millar, E.A., et al., "Angiotensin II potentiates methacholine-induced bronchoconstriction in human airway both in vitro and in vivo," Eur. Respir. J., 8(11):1838-1841, European Respiratory Society, Switzerland (1995).
Nagamitsu, A., et al., "Elevating blood pressure as a strategy to increase tumor-targeted delivery of macromolecular drug SMANCS: cases of advanced solid tumors," Jpn J Clin Oncol, 39(11):756-766, Oxford University Press, United Kingdom (2009).
NCBI Database, PubChem Compound Database, PubChem CID: 172198.
NCBI Database, PubChem Compound Database, PubChem CID: 73354658.
Onohara, S., et al., "Intra-arterial cis-platinum infusion with sodium thiosulfate protection and angiotensin II induced hypertension for treatment of hepatocellular carcinoma," Acta Radiol, 29(2):197-202 Sage Publications, United States (1988).
Orfanos, S.E., et al., "Assay of Pulmonary Microvascular Endothelial Angiotensin-converting Enzyme In Vivo: Comparison of Three Probes," Toxicol Appl Pharmacol, 124(1): 99-111 Elsevier, Netherlands (1994).
Orfanos, S., et al., "Pulmonary Capillary Endothelium-bound Angiotensin-converting Enzyme Activity in Acute Lung Injury," Circulation, 102(16): 2011-2018, American Heart Association, United States (2000).
Orfanos, S., et al., "Pulmonary Capillary Endothelium-bound Angiotensin-converting Enzyme Activity in Humans," Circulation, 99(12):1593-1599, American Heart Association, United States (1999).
Pariente, E., et al., "Acute Effects of Captopril on Systemic and Renal Hemodynamics and on Renal Function in Cirrhotic Patients with Ascites," Gastroenterology, 88(5): 1255-1259 Elsevier, Netherlands (1985).
Pickering, T., et al., "Recommendations for blood pressure measurement in humans and experimental animals: Part 1: Blood pressure measurement in humans: A Statement for professionals from the Subcommittee of Professional and Public Education of the American Heart Association Council on High Blood Pressure Research," Circulation, 111: 697-716, American Heart Association, United States (2005).
Saino, A., et al., "Intracoronary angiotensin II potentiates coronary sympathetic vasoconstriction in humans," Circulation 96(1):148-153, American Heart Association, United States (1997).

(56) References Cited

OTHER PUBLICATIONS

Swartz et al., "Converting Enzyme Inhibition in Essential Hypertension: The Hypotensive Response does Not Reflect only Reduced Angiotensin II Formation," Hypertension, 1: 106-111, American Heart Association, United States (1979).
Vincent, R., et al., "Prophylactic angiotensin II infusion during spinal anesthesia for elective cesarean delivery," Anesthesiology, 88(6):1475-1479 Lippincott Williams & Wilkins, United States (1998).
Vos, P., et al., "Efficacy of intrarenal ACE-inhibition estimated from the renal response to angiotensin I and II in humans," Kidney Int, 47(1):274-281, Elsevier, Netherlands (1995).
Vos, P., et al., "The origin of urinary angiotensins in humans," J Am Soc Nephrol, 5(2):215-223, American Society of Nephrology, United States (1994).
Wadei, H., et al., "Hepatorenal Syndrome: Pathophysiology and Management," Clin J Am Soc Nephrol, 1: 1066-1079, American Society of Nephrology, United States (2006).
Ware, L., et al., "The Acute Respiratory Distress Syndrome," N Engl J Med, 342(18):1334-1349, Massachusetts Medical Society, United States (2000).
Weber, K., "Extracellular matrix remodeling in heart failure: a role for De Novo angiotensin II generation," Circulation, 96(11):4065-4082, American Heart Association, United States (1997).
Abuelo, J., "Normotensive Ischemic Acute Renal Failure," N Engl J Med, 357(8):797-805, Massachusetts Medical Society, United States (2007).
Leone. M., et al., "Optimizing mean arterial pressure in septic shock: A critical reappraisal of the literature," Critical Care 19:101, 1-7, BioMed Central, (2015).
Asfar, P., et al., "Angiotensin-II: more than just another vasoconstrictor to treat septic shock-induced hypotension?" Crit Care Med, 42(8): 1961-1963, Lippincott Williams & Wilkins, United States (2014).
Bachem, H-1705, Angiotensin II, downloaded online on Dec. 15, 2014, accessed from URL: http://shop.bachem.com/h-1705-1.html.
Bachem, Angiotensins and Related Peptides, downloaded on Sep. 22, 2015, accessed from URL<http://www.archive.org/web/20100730002830/http://shop.bachem.com/ep6sf/peptides-and-biochemicals/angiotensins-and-related-peptides/c4750-c4771-p2.html?sorter=sortNumber-asc>.
Chemmwatch, Angiotensin II, 5-L-isoleucine-, Acetate (Salt), downloaded online on Mar. 5, 2015, accessed from URL: http://www.chemwatch.net/product/angiotensin-ii-5-l-isoleucine-acetate-salt.
Johnston, et al., "Outcomes of military patients treated at the UK Royal Centre for Deference Medicine 2007 to 2013," Critical Care, 18 (Supp 1): P57, BioMed Central, United Kingdom (2014).
Kimmoun et al., "Angiotensin II: a new approach for refractory shock Management?," Crit Care, 18(6): 694, BioMed Central, United Kingdom (2014).
Leibly et al., "Stabilizing additives added during cell lysis aid in the solubilization of recombinant proteins," PLoS One 7(12): e52482, pp. 1-13 Public Library of Science, United States, (2012).
Bhimma, et al., "Pediatric Hepatorenal Syndrome Workup," Medscape Drugs, Disease & Procedures, accessed online on Jan. 2, 2015 from URL: http://emedicine.medscape.com/article/907429-workup (2011).
Valdes, G., et al., "Administration of Angiotensin II and a Bradykinin B2 Receptor Blocker in Midpregnancy Impairs Gestational Outcome in Guinea Pigs," Reproductive Biology and Endocrinology, 12(49): 1-8, BioMed Central, United Kingdom (2014).
Boehm, "Angiotensin-Converting Enzyme 2—A New Cardiac Regulator," N Engl J Med, 347(22): 1795-1797, Massachusetts Medical Society, United States (2002).
Oney, T., et al., "Effect of angiotensin infusion during pregnancy on fetal heart rate and on fetal activity," Eur. J. Obstet. Gynecol. Reprod. Biol.;13(3):133-137, Elsevier, Netherlands (1982).
Catanzaro F., et al., "Angiotensin-Infusion Test. Correlation with renin activity in peripheral venous blood," Arch Intern Med. ;122(1):10-17, American Medical Association, United States (1968).

Cook C.M., et al., "Maternal angiotensin sensitivity and fetal Doppler umbilical artery flow waveforms," Br J Obstet Gynaecol.; 98(7):698-702, Wiley & Sons, United States (1991).
Fridman K.U., et al., "Influence of AT1 receptor blockade on blood pressure, renal haemodynamics and hormonal responses to intravenous angiotensin II infusion in hypertensive patients," Blood Press. 11(4):244-252, Taylor & Francis, United Kingdom (2002).
Gordon R.D., et al., "A renin-secreting tumour sensitive to changes in central blood volume (presumably via sympathetics) but not to circulating angiotensin II," Clin Exp Pharmacol Physiol. 17(3):185-189, Wiley & Sons, United States (1990).
Katayama K., et al., "Dynamic determinants of left ventricular early diastolic filling in old myocardial infarction," Jpn Circ J. 56(7):750-758, Japanese Circulation Society, Japan (1992).
Larsson P.T., et al., "Acute effects of angiotensin II on fibrinolysis in healthy volunteers," Blood Coagulation Fibrinolysis 10(1):19-24, Lippincott Williams and Wilkins, United Kingdom (1999).
Matsuda Y., et al., "Change of left atrial systolic pressure waveform in relation to left ventricular end-diastolic pressure," Circulation 82(5):1659-1667, AHA Journals, United States (1990).
Rouine-Rapp K., et al., "Effect of enalaprilat on postoperative hypertension after surgical repair of coarctation of the aorta," Pediatr Crit Care Med. 4(3):327-332, Society of Critical Care Medicine, United States (2003).
Schachinger H., et al., "Angiotensin II decreases the renal MRI blood oxygenation level-dependent signal. Hypertension," 47(6):1062-1066, American Heart Association, United States (2006).
Seidelin P.H., et al., "The effect of angiotensin II on haemodynamic and plasma noradrenaline responses to tyramine infusion in man," Eur J Clin Pharmacol. 41(2):119-123, Springer Science + Business, Germany (1991).
Vingerhoedt N.M., et al., "Haemodynamic and pulse wave responses to intravenous infusions of angiotensin II during chronic telmisartan therapy in normal volunteers," J Renin Angiotensin Aldosterone Syst. 4(4):244-248, Sage Publications, United States (2003).
Widgren B.R., et al., "Low-dose angiotensin II increases glucose disposal rate during euglycemic hyperinsulinemia," Am J Hypertens. 6(10):892-895 Oxford University Press, United Kingdom (1993).
Gordon R.D., et al., "Angiotensin-responsive aldosterone-producing adenoma masquerades as idiopathic hyperaldosteronism (IHA: Adrenal hyperplasia) or low-renin essential hypertension," J Hypertens Suppl. 5(5):S103-S106, Wolters Kluwer, United Kingdom (1987).
Gordon R.D., et al., "A new Australian kindred with the syndrome of hypertension and hyperkalaemia has dysregulation of atrial natriuretic factor," J Hypertens 6(Suppl. 4):S323-S326, Wolters Kluwer, United Kingdom (1988).
McGibney D., et al., "Observations on the mechanism underlying the differences in exercise and isoprenaline tachycardia after cardioselective and non-selective beta-adrenoceptor antagonists," Br J Clin Pharmacol. 15(1):15-19, Wiley-Blackwell, United Kingdom (1983).
Merillon J.P., et al., "Forward and backward waves in the arterial system, their relationship to pressure waves form," Eur Heart J. 4(Suppl G):13-20, Oxford University Press, United Kingdom (1983).
Ogihara T., et al., "Clinical efficacy and tolerability of candesartan cilexetil," and "Discussion 1 New refinements in the approach to hypertension management," J Hum Hypertens. 13(Suppl 1):S27-S31 and S33-S34, Nature Publishing Group, United Kingdom (1999).
Shen W.F., et al., "Evaluation of relationship between myocardial contractile state and left ventricular function in patients with aortic regurgitation," Circulation 71(1):31-38, AHA Journals, United States (1985).
Sowers J.R., et al., "Effects of dietary sodium on circadian rhythm and physiological responses of 18-hydroxycorticosterone," Clin Sci (Lond). 64(3):295-301, Portland Press, United Kingdom (1983).
Woodland E., et al., "Hypertension corrected and aldosterone responsiveness to renin-angiotensin restored by long-term dexamethasone in glucocorticoid-suppressible hyperaldosteronism," Clin Exp Pharmacol Physiol. 12(3):245-248, John Wiley & Sons, United States (1985).
Bentsen N., et al., "Chronically impaired autoregulation of cerebral blood flow in long-term diabetics," Stroke 6(5):497-502, American Heart Association, United States (1975).

(56) References Cited

OTHER PUBLICATIONS

Cokkinos D.V., et al., "Constancy of pressure-rate product in pacing-induced angina pectoris," Br Heart J. 38(1):39-42, BMJ Group, United Kingdom (1976).
Enevoldsen E.M., et al., "Autoregulation and CO2 responses of cerebral blood flow in patients with acute severe head injury," J Neurosurg. 48(5):689-703, American Association of Neurological Surgeons, United States (1978).
Fraser R., et al., "The acute effect of angiotensin II on adrenal and anterior pituitary function in normal subjects and subjects with primary hyperaldosteronism," Prog Biochem Pharmacol. 17:14-19, Karger Publishers, Switzerland (1980).
Goldsmith S.R., et al., "Angiotensin II and sympathetic activity in patients with congestive heart failure," J Am Coll Cardiol. 1993;15(5):1107-1113, Elsevier, Netherlands (1993).
Hogewind B.L., et al., "Bartter's syndrome: An autosomal recessive disorder? Study of four patients in one generation of the same pedigree and their relatives," Acta Med Scand. 209(6):463-467, John Wiley & Sons, United States (1981).
Kaulhausen H., et al., "Decrease of vascular angiotensin sensitivity by L-dopa during human pregnancy," Am J Obstet Gynecol. 140(6):671-675, Elsevier, United States (1981).
Schaison G., et al., "Angiotensin and adrenal steroidogenesis: Study of 21-hydroxylase-deficient congenital adrenal hyperplasia," J Clin Endocrinol Metab., 51(6):1390-1394, Endocrine Society, United States (1980).
Semple P.F., et al., "Suppression of plasma ACTH concentration by angiotensin II infusion in normal humans and in a subject with a steroid 17 alpha-hydroxylase defect," Clin Endocrinol (Oxf). 10(2):137-144, John Wiley & Sons, United States (1979).
Speckart P., et al., "The effect of angiotensin II and indomethacin on immunoreactive prostaglandin "A" levels in man," Prostaglandins. 1976;11(3):481-488, Elsevier, Netherlands (1976).
Ahmed S.S., et al., "The effect of angiotensin on myocardial contractility," J Clin Pharmacol, 15(4 Pt 1):276-285, John Wiley & Sons, United States (1975).
Brown M.A., et al., "The effects of intravenous angiotensin II upon blood pressure and sodium and urate excretion in human pregnancy," J Hypertens., 6(6):457-464, Lippincott Williams & Wilkins, United States (1988).
Frolich J.C., et al., "Urinary prostaglandins. Identification and origin," J Clin Invest, 55(4):763-770, American Society for Clinical Investigation, United States (1975).
Henriksen O., et al., "The effect of induced arterial hypertension upon regional blood flow in subcutaneous tissue in patients with arterial insufficiency of the legs," Scand J Clin Lab Invest., 35(2):115-120, Taylor & Francis, United Kingdom (1975).
Koch B., et al., "The influence of angiotensin infusion on the urine composition in individual kidney function tests," Can Med Assoc J., 104(10):905-907, Canadian Medical Association, Canada (1971).
Mehrotra, M.P., et al., "Angiotensin Infusion Test in the Diagnosis of Renal Hypertension," Journal of the Association of Physicians of India 22(4):289-292, Association of Physicians of India, India (1974).
Mendelsohn F.A., et al., "Renin, angiotensin II, and adrenal corticosteroid relationships during sodium deprivation and angiotensin infusion in normotensive and hypertensive man," Circ Res. 31(5):728-739, Lippincott Williams & Wilkins, United States (1972).
Oelkers W., et al., "Arterial angiotensin II and venous immunoreactive material before and during angiotensin infusion in man," Clin Sci. 43(2):209-218. Portland Press, United Kingdom (1972).
Parmley W.W., et al., "Dissociation between indices of pump performance and contractility in patients with coronary artery disease and acute myocardial infarction," Chest. 67(2):141-146, American College of Chest Physicians, United States (1975).
Payne R.M., et al., "Comparison of isometric exercise and angiotensin infusion as stress test for evaluation of left ventricular function," Am J Cardiol. 31(4):428-433, Elsevier, Netherlands (1973).
Rado J.P., et al., "Studies on the sites of action of ethacrynic acid and furosemide during angiotensin infusion," J Clin Pharmacol 10(6):375-381, John Wiley & Sons, United States (1970).
Ronan J.A., Jr, et al., "The angiotensin infusion test as a method of evaluating left ventricular function," Am Heart J. 89(5):554-560, Elsevier, Netherlands (1975).
Rado J.P., et al., "Effects of ethacrynic acid on specific renal functions without and during angiotensin infusion in man," Arch Int Pharmacodyn 186(1):142-154, Elsevier, Netherlands (1970).
Fukuchi, S., and Nakajima, K., "Diagnostic Value of Plasma Renin Activity and Plasma Angiotensin II in Renovascular Hypertension," Japanese Circulation Journal 39(7):823-827, Kyoto, Japanese Circulation Society(1975).
Brod, J., et al., "Comparison of Haemodynamic Effects of Equipressor Doses of Intravenous Angiotensin and Noradrenaline in Man," Clinical Science 36(2):161-172, Portland Press on behalf of the Medical Research Society and the Biochemical Society, United Kingdom (1969).
Genest, J., "The Value of the Angiotensin Infusion Test in the Diagnosis of True Renovascular Hypertension," American Heart Journal 76(4):443-444, Mosby, United States (1968).
Jezek V., et al., "Haemodynamic Reaction to Exercise and Increased Afterload in the Detection of Right Heart Failure in Pulmonary Diseases," Cor et Vasa 22(4):272-280, Elsevier, Amsterdam (1980).
Spark, R.F., et al., "Activation of Aldosterone Secretion in Primary Aldosteronism," The Journal of Clinical Investigation 48(1):96-104, American Society for Clinical Investigation, United States(1969).
Oelkers, W., et al., "Effect of Prolonged Low-Dose Angiotensin II Infusion on the Sensitivity of Adrenal Cortex in Man," Circulation Research 36 and 37 (Supp) 1):149-156, Lippincott Williams & Wilkins, United States(1975).
Klemm, S.A., et al., "Altering Angiotensin Levels by Administration of Captopril or Indomethacin, or by Angiotensin Infusion, Contributes to an Understanding of Atrial Natriuretic Peptide Regulation in Man," Clinical and Experimental Pharmacology and Physiology 15(4):349-355, Wiley-Blackwell, Oxford, England (1988).
Chobanian, A.V., et al., "The Seventh Report of the Joint National Committee on Prevention, Detection, Evaluation, and Treatment of High Blood Pressure: The JNC 7 report," Journal of the American Medical Association 289(19):2560-2572, American Medical Assn., United States (2003).
Bianco, J.A., et al., "Angiotensin Infusion Effects on Left Ventricular Function. Assessment in Normal Subjects and in Patients with Coronary Disease," Chest 77(2):172-175, Elsevier, United States (1980).
Merillon, J.P., et al., "Aortic Input Impedance in Normal Man and Arterial Hypertension: It's Modification during Changes in Aortic Pressure," Cardiovascular Research 16(11):646-656, Oxford Journals, Oxford (1982).
Sluiter, H.E., et al., "The Natriuretic Effect of the Dihydropyridine Calcium Antagonist Felodipine: A Placebo-Controlled Study Involving Intravenous Angiotensin II in Normotensive Volunteers," Journal of Cardiovascular Pharmacology 10(Suppl 10):S154-S161, Lippincott Williams & Wilkins, United States (1987).
"Angiotensin in Septic Kidney Injury Trial," accessed on Jan. 8, 2019, available online at https://anzctr.org.au/Trial/Registration/TrialReview.aspx?id=2037&isClinicalTrial=True, 6 pages (Aug. 7, 2008).
"Angiotensin in Septic Kidney Injury Trial (ASK-IT)," accessed on Jan. 8, 2019, available online at https://clinicaltrials.gov/ct2/show/NCT00711789, 7 pages (Jul. 9, 2008).
English language translation of Office Action for Chinese Patent Application No. 201480075899.1, dated May 6, 2020, 12 pages.
Song; Y. et al., "The Relationship and Significance of Angiotensin II and Nitric Oxide in Children with Septic Shock," Chinese Journal of Pediatric Surgery 25(1):89-91, (2004).
Badin, J., et al., "Relation between mean arterial pressure and renal function in the early phase of shock: a prospective, explorative cohort study," Crit. Care, 15:R135, pp. 1-12, BioMed Central, United Kingdom(2011).
Ferreira, F., et al., "Serial Evaluation of the SOFA Score to Predict Outcome in Critically Ill Patients," JAMA, 286(14): 1754-1758, American Medical Association, United States (2001).

(56) References Cited

OTHER PUBLICATIONS

Lehman, Li-wei, et al., "Hypotension as a Risk Factor for Acute Kidney Injury in ICU Patients," Computing in Cardiology, 37:1095-1098, Cardiology and Cardiovascular Medicine, United States (2010).

Khanna, A., et al., "Angiotensin II for the Treatment of Vasodilatory Shock," N Engl J Med, 377:419-430, Massachusetts Medical Society, United States (2017).

Tumlin, J., et al., "Outcomes in Patients with Vasodilatory Shock and Renal Replacement Therapy Treated with Intravenous Angiotensin II," Critical Care Medicine, 46(6):949-957, BioMed Central, United Kingdom (2018).

Extended European Search Report for European Application No. 17736407.2, European National Stage Application of PCT/US2017/0120438, European Patent Office, Germany, dated Jul. 2, 2019, 7 pages.

Zambelli, V., et al., "Angiotensin-(1-7) improves oxygenation, while reducing cellular infiltrate and fibrosis in experimental Acute Respiratory Distress Syndrome," Intensive Care Medicine Experimental, 3(8): pp. 1-17 (2015).

\* cited by examiner

SEQUENCE LISTING

```
<160> NUMBER OF SEQ ID NOS: 8

<210> SEQ ID NO 1
<211> LENGTH: 8
<212> TYPE: PRT
<213> ORGANISM: Unknown
<220> FEATURE:
<223> OTHER INFORMATION: Description of Unknown: Angiotensin II
      peptide

<400> SEQUENCE: 1

Asp Arg Val Tyr Ile His Pro Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Val Tyr Val His Pro Phe
1               5
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Arg Val Phe Ile His Pro Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Tyr Ile His Pro Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Arg Val Tyr Tyr Val His Pro Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Arg Val Tyr Ile His Pro Ile
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Arg Val Tyr Ile His Pro Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (4)..(4)
<223> OTHER INFORMATION: diiodo-Tyr

<400> SEQUENCE: 8

Asn Arg Val Tyr Ile His Pro Phe
1               5
```

ANGIOTENSIN II ALONE OR IN COMBINATION FOR THE TREATMENT OF HYPOTENSION

This application is a continuation of U.S. patent application Ser. No. 16/135,608, filed Sep. 19, 2018, which is a continuation of U.S. patent application Ser. No. 15/909,617, filed Mar. 1, 2018, which is a continuation of U.S. patent application Ser. No. 14/941,301, filed Nov. 13, 2015, which is a continuation of U.S. patent application Ser. No. 14/575,127, filed on Dec. 18, 2014, and claims the benefit of the filing date of U.S. Provisional Applications 61/917,576, filed Dec. 18, 2013, and U.S. Provisional Application 61/955,706, filed Mar. 19, 2014, each of which is incorporated by reference in their entirety herein.

SEQUENCE LISTING

The instant application contains a Sequence Listing which has been submitted electronically in ASCII format and is hereby incorporated by reference in its entirety. Said ASCII copy, created on Dec. 18, 2014, is named 123585_375374_SL.txt and is 2,088 bytes in size.

BACKGROUND INFORMATION

Critically ill patients with shock requiring vasopressors are at a high risk of death. High output shock (also known as distributive shock) is the most common form of shock, and is often caused by sepsis [1]. When shock is treated with vasopressors, two main classes of vasopressors are in the intensivists' armamentarium: catecholamines and vasopressin type peptides [1]. Currently, no specific type of vasopressor (e.g. norepinephrine, vasopressin, dopamine) compared to another vasopressor has been shown to improve outcome [2]. All vasopressors have limitations and potential side effects. Patients treated with catecholamines for shock often develop tachyphylaxis thereby limiting the utility of these agents, and high doses of catecholamines can cause direct cardiotoxicity [3]. The toxic potential of catecholamines has been recently demonstrated in a randomized clinical trial of septic shock patients treated norepinephrine [4]. In this study, beta-blockade with esmolol was shown to improve survival in these patients by decreasing the heart rate. Thus, vasopressors that are not inotropes or chronotropes may be useful in patients with shock. One such vasopressor is vasopressin, which is most commonly used as an adjuvant with catecholamines. Vasopressin has been shown to improve outcomes in patients with less severe septic shock, but has toxicity (e.g. cardiac and mesenteric ischemia) at high doses and interacts with hydrocortisone [5]. In high-output shock, the patients are critically ill and mean arterial pressure cannot be maintained without vasopressors. High-output shock is defined as a cardiovascular Sequential Organ Function Assessment (SOFA) score of greater than or equal to 3 or 4 as well as a cardiac index of >2.4 liters/min/BSA 1.73 m$^2$ [10]. In high-output shock, if blood pressure cannot be maintained, it is uniformly fatal. In patients that cannot maintain their blood pressure, the addition of a 'rescue' vasopressor in this setting could be useful.

A subset of patients with shock (including high-output shock and other types of shock) are catecholamine-resistant. That is, they are unresponsive (do not exhibit an appropriate increase in blood pressure) in response to treatment with a dose of a catecholamine equivalent to a dose of at least 0.2 mcg/kg/min of norepinephrine.

Angiotensin II (sometimes referred to herein as ATII) is a naturally occurring peptide hormone with endocrine, autocrine, paracrine, and intracrine hormonal effects. It is a potent direct vasoconstrictor, constricting both arteries and veins and increasing blood pressure [6]. It has a half-life in circulation of approximately 30 seconds, but while in tissue, its half-life may be as long as 15-30 minutes. ATII increases secretion of ADH and ACTH, and may potentiate sympathetic effects by direct action on postganglionic sympathetic fibers. It also acts on the adrenal cortex, causing it to release aldosterone [6,7]. High doses of angiotensin II have been reported to induce adverse side effects, including for example, mesenteric ischemia and bronchospasm.

DESCRIPTION

Figure 1:
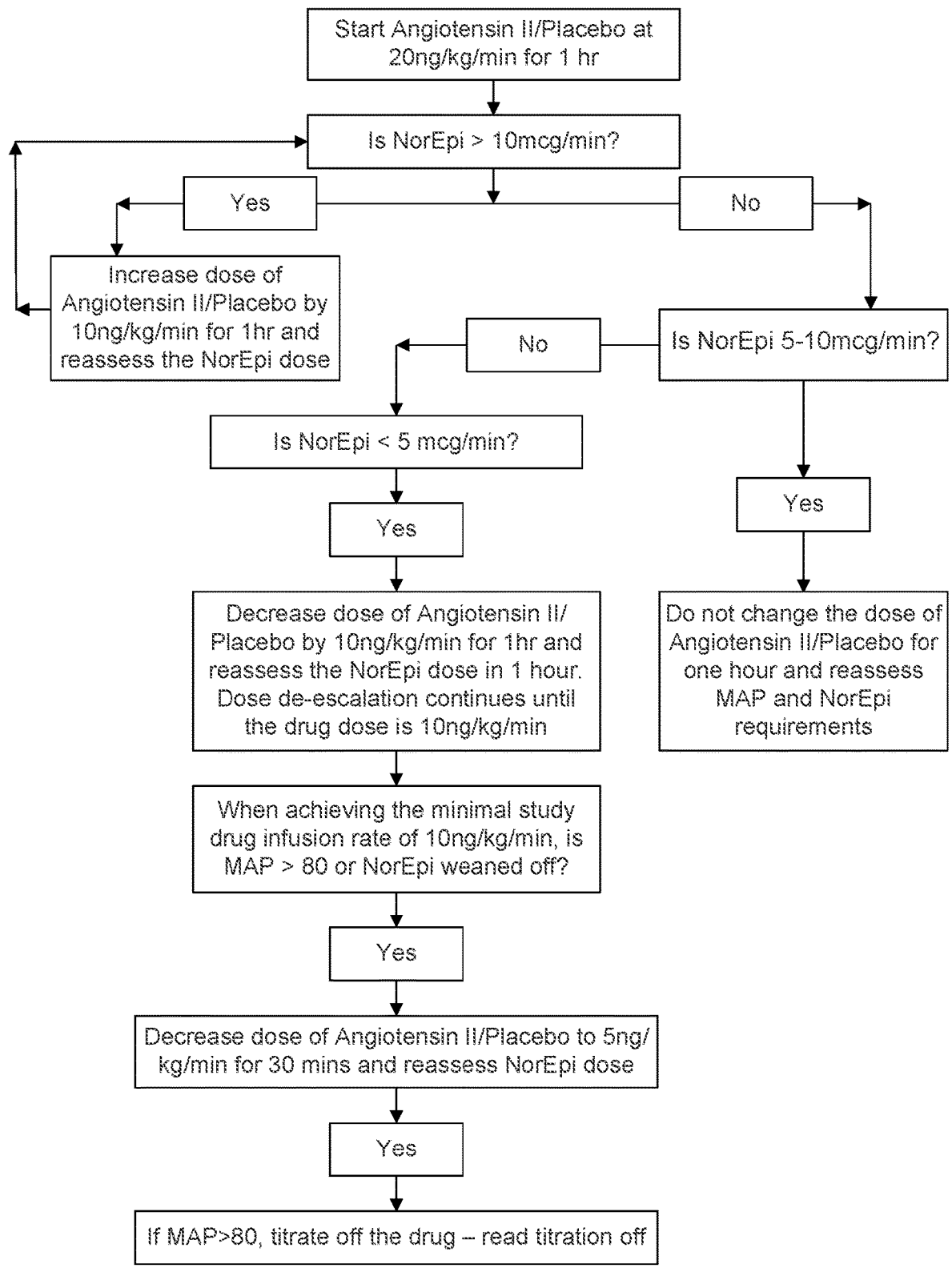
FIG. 1 shows study drug titration protocol.

This invention relates, inter alia, to the surprising finding by the present inventors that in response to the administration of very low doses of angiotensin II to subjects having hypotension, e.g., exhibiting distributive shock (high output shock), the blood pressure can be raised to a normal level (e.g., a mean arterial pressure (MAP) of about 65 mm Hg or higher) and can be maintained at this level, even in the absence of, or with low doses of, other agents such as vasopressin or catecholamines (e.g., norepinephrine) that are generally administered to such subjects as the standard of care. The reduction or elimination of a need to administer a catecholamine (e.g., norepinephrine) is sometimes referred to herein as a catecholamine-sparing (norepinephrine-sparing) effect. Administering low doses of angiotensin II and of a catecholamine such as norepinephrine reduces undesirable side effects brought about by these drugs. High doses of catecholamines can be toxic, and the blunting of these toxic effects has been associated with improved survival in patient with shock. Maintenance of blood pressure during shock is critical to survival. In addition to raising blood pressure, heart rate and hemodynamics are improved or remain stable following administration of the low doses of angiotensin II.

Definitions

As used herein, the singular forms "a," "an," and "the" include plural referents unless the context clearly dictates otherwise. For example, treatment with "a" catecholamine as used above includes treatment with one or more types of catecholamine.

The term "about" as used herein, means within about 10% of the indicated value, preferably plus or minus 5% of the indicated value.

The term "angiotensin II" may refer to Asp-Arg-Val-Tyr-Ile-His-Pro-Phe [SEQ ID NO: 1] also called 5-isoleucine angiotensin II. SEQ ID NO: 1 is an octa-peptide naturally present in humans and other species, such as equines, hogs, etc. Isoleucine may be substituted by valine to result in 5-valine angiotensin II, Asp-Arg-Val-Tyr-Val-His-Pro-Phe [SEQ ID NO: 2]. Other angiotensin II analogues such as [Asn$^1$-Phe$^4$]-angiotensin II [SEQ ID NO: 3], hexapeptide Val-Tyr-Ile-His-Pro-Phe [SEQ ID NO: 4], nonapeptide Asn-Arg-Val-Tyr-Tyr-Val-His-Pro-Phe [SEQ ID NO: 5], [Asn$^1$-

Ileu$^5$-Ileu$^8$]-angiotensin II [SEQ ID NO: 6], [Asn$^1$-Ileu$^5$-Ala$^8$]-angiotensin II [SEQ ID NO: 7], and [Asn$^1$-diiodoTyr$^4$-Ileu$^5$]-angiotensin II [SEQ ID NO: 8] may also be used. Angiotensin II may be synthesized, for example, by solid phase peptide synthesis to incorporate modifications, such as C-terminal amidation. C-terminal acetate groups may also be added. The term "angiotensin II", without further specificity, is intended to refer to any of these various forms, as well as combinations thereof.

The term "catecholamine", as used herein, refers to dopamine, norepinephrine, epinephrine, phenylephrine, ephedrine and their prodrugs, structural analogs, or derivatives that induce similar physiological effects in humans, e.g., raise mean arterial pressure in healthy human subjects. In certain embodiments, the catecholamine may be dopamine, norepinephrine, epinephrine, ephedrine or phenylephrine.

The term "catecholamine-resistant hypotension" as used herein refers to patients who require more than 15 μg/kg/min of dopamine, 0.1 μg/kg/min norepinephrine, or 0.1 μg/kg/min epinephrine as a vasopressor. Dopamine, norepinephrine, and epinephrine may be administered at rates higher than 15 μg/kg/min, 0.1 μg/kg/min, or 0.1 μg/kg/min, respectively, but elevated rates correlate with increased mortality.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The term "including" is used to mean "including but not limited to." "Including" and "including but not limited to" are used interchangeably.

The term "mean arterial pressure" or "MAP" refers to the average arterial pressure during a single cardiac cycle.

As used herein, a "subject" or "patient" refers to any animal (e.g., a mammal), including human, non-human primate, rodent, etc., which is to the recipient of a particular treatment. Typically, the terms "subject" and "patient" are used interchangeable herein in reference to a human subject.

Angiotensin II Therapeutics

Angiotensin II is a peptide hormone naturally produced by the body that regulates blood pressure via vasoconstriction and sodium reabsorption. Hemodynamic effects of angiotensin II administration have been the subject of numerous clinical studies, demonstrating significant effects on systemic and renal blood flow (Harrison-Bernard, L. M., *The renal renin-angiotensin system.* Adv Physiol Educ, (2009) 33(4): p. 270-74). Angiotensin II is a hormone produced by the renin angiotensin aldosterone system (RAAS) that modulates blood pressure via regulation of vascular smooth muscle tone and extracellular fluid homeostasis. Angiotensin II mediates its effects on the vasculature by inducing vasoconstriction and sodium retention. In addition to its systemic effects, angiotensin II has a pronounced effect on the efferent arterioles of the kidney, maintaining glomerular filtration when blood flow is decreased. Angiotensin II also regulates sodium reabsorption in the kidney by stimulating Na+/H+ exchangers in the proximal tubule and inducing the release of aldosterone and vasopressin (Harrison-Bernard, L. M., *The renal renin-angiotensin system.* Adv Physiol Educ, 2009. 33(4): p. 270-4.).

The sequence of angiotensin II used in the compositions and methods disclosed herein may be homologous to the sequences of angiotensin II described above. In certain aspects, the invention includes isolated, synthetic, or recombinant amino acid sequences that are at least 80%, 85%, 90%, 95%, 97%, 98%, 99% or 100% identical to SEQ ID NO: 1, 2, 3, 4, 5, 6, 7, and/or 8. Any such variant sequences may be used in place of an angiotensin II as described in the preceding paragraph.

In some aspects, the angiotensin II may be selected from 5-valine angiotensin II, 5-valine angiotensin II amide, 5-L-isoleucine angiotensin II, and 5-L-isoleucine angiotensin II amide, or a pharmaceutically acceptable salt thereof, preferably manufactured under current good manufacturing conditions (cGMP). In some aspects, the composition may include different forms of angiotensin II in different percentages, e.g., a mixture of hexapeptide and nonapeptide angiotensin. The composition comprising angiotensin II may be suitable for parenteral administration, e.g., for injection or intravenous infusion.

Similarly, an angiotensin II therapeutic may be used as any suitable salt, deprotected form, acetylated form, deacetylated form, and/or prodrug form of the above-mentioned peptides, including pegylated forms of the peptides or conjugates as disclosed in U.S. Pat. No. 7,666,408 (incorporated by reference). The term "prodrug" refers to any precursor compound which is able to generate or to release the above-mentioned peptide under physiological conditions. Such prodrugs may be larger peptides which are selectively cleaved in order to form the peptide of the invention. For example, in some aspects, the prodrug may be angiotensin I or its homologues that may result in angiotensin II by the action of certain endogenous or exogenous enzymes. Further prodrugs include peptides with protected amino acids, e.g., having protecting groups at one or more carboxylic acid and/or amino groups. Suitable protecting groups for amino groups are the benzyloxycarbonyl, t-butyloxycarbonyl (BOC), fluorenylmethyloxycarbonyl (FMOC), formyl, and acetyl or acyl group. Suitable protecting groups for the carboxylic acid group are esters such as benzyl esters or t-butyl esters. The present invention also contemplates the use of angiotensin II and/or precursor peptides having amino acid substitutions, deletions, additions, the substitutions and additions including the standard D and L amino acids and modified amino acids, such as, for example, amidated and acetylated amino acids, wherein the therapeutic activity of the base peptide sequence is maintained at a pharmacologically useful level.

Indications

Methods of the invention can be used to treat a subject exhibiting a variety of types of shock, such as, e.g., high output shock, septic shock or shock from cardiac arrest or cardiogenic shock. Other conditions that can be treated with the indicated low doses of angiotensin II include acute kidney injury (MCI), hepato-renal syndrome (HRS) and variceal bleeding.

Doses of the Therapeutically Effective Substance

In general, angiotensin II increases blood pressure, and patients who are hypotensive may require larger doses to exhibit pressor responses similar to those observed in normal patients. The composition including the angiotensin therapeutic (e.g., angiotensin II) can be administered at a rate sufficient to achieve a target blood pressure. For example, a patient may be coupled to a monitor that provides continuous, periodic, or occasional measurements of MAP.

The precise amount of a drug to be administered to a mammal for the treatment of hypotension and shock is dependent on numerous factors known to one skilled in the art, such as, the agent to be administered, the general condition of the patient, the condition to be treated, the desired duration of use, the type of mammal, the method of administration etc.

The dose of angiotensin II can be administered at a rate of from about 0.25 ng/kg/min to about 100 ng/kg/min, e.g. from about 10 ng/kg/min to about 50 ng/kg/min, from about 20 ng/kg/min to about 40 ng/kg/min, from about 0.25 ng/kg/min to about 20 ng/kg/min, from about 0.25 ng/kg/min to about 10 ng/kg/min, from about 0.25 ng/kg/min to about 5 ng/kg/min, from about 1.25 ng/kg/min to about 20 ng/kg/min, about 1.25 ng/kg/min to about 10 ng/kg/min, or from about 1.25 ng/kg/min to about 5 ng/kg/min. In embodiments of the invention, the dose is about 0.25 ng/kg/min, about 0.5 ng/kg/min, about 1 ng/kg/min, about 1.25 ng/kg/min, about 1.5 ng/kg/min, about 2 ng/kg/min, about 2.5 ng/kg/min, about 3 ng/kg/min, about 3.5 ng/kg/min, about 4 ng/kg/min, about 4.5 ng/kg/min, about 5 ng/kg/min, about 5.5 ng/kg/min, about 6 ng/kg/min, about 7.5 ng/kg/min or about 10 ng/kg/min.

Figure 4:
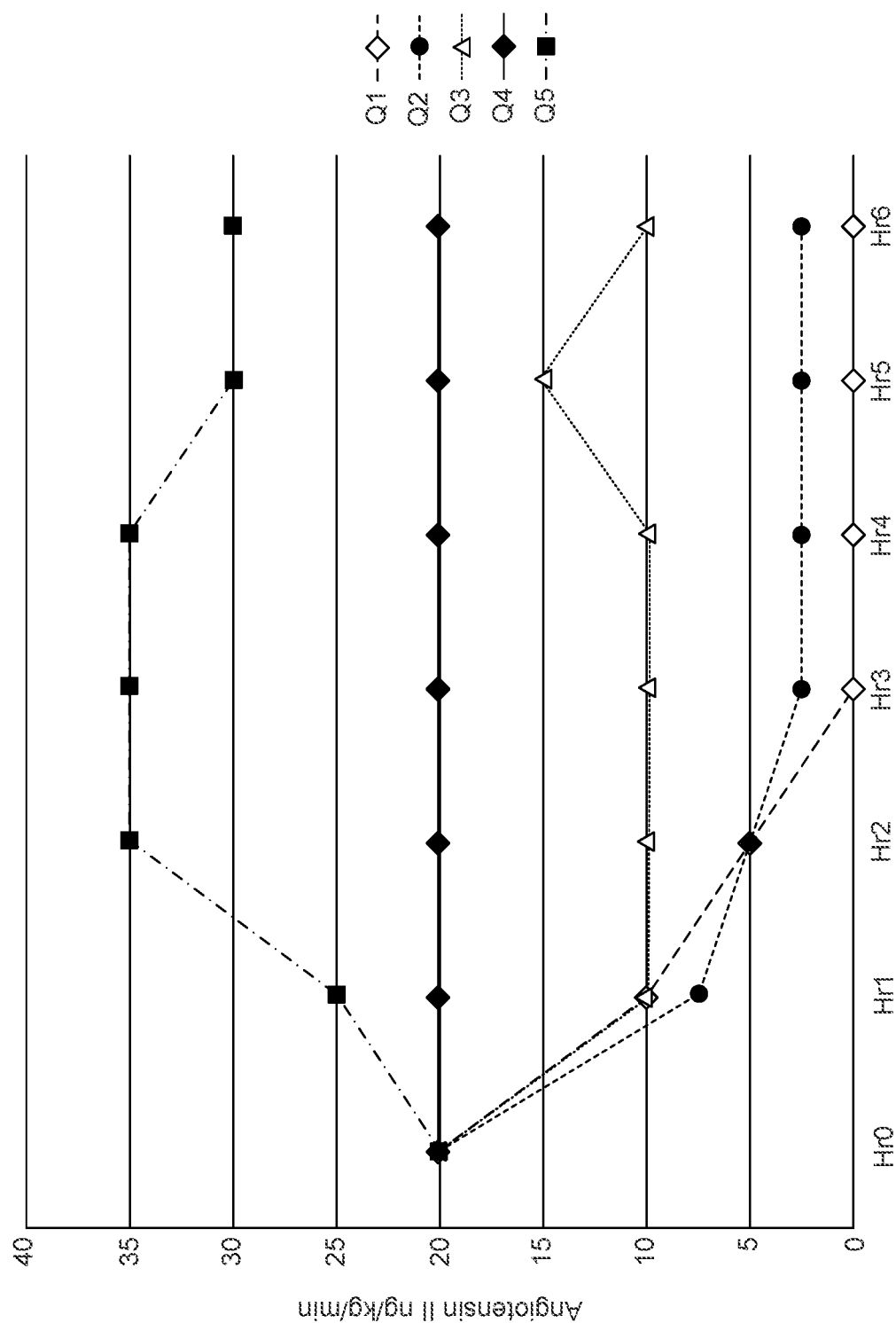
FIG. 4 shows Angiotensin II Dose Titration—Quintiles

FIG. 4 and the Examples indicate that subjects with high output shock requiring high doses of catecholamine (in the exemplified case, norepinephrine) who are administered as little as 1 or 2.5 ng/kg/min of angiotensin II show an increase in blood pressure and maintain it, even in the absence of, or with very low doses of, norepinephrine. In the study illustrated in FIG. 4, subjects requiring high doses of norepinephrine (>0.2 mcg/kg/min) responded to low dose angiotensin II, such that the norepinephrine was discontinued, and the effect of angiotensin II converted these patients from hypotensive to hypertensive.

The dose administration can last from about 0.25 hours to about 120 hours, e.g., from about 1 hour to about 7 hours, 2 hours to about 6 hours, or about 3 hours to about 5 hours.

The therapeutic regimen can be started within, e.g., 1 hour, 2 hours, 4 hours, 6 hours, 12 hours, 24 hours, 48 hours, or 72 hours, after the onset of acute symptoms.

Formulations

Suitable formulations (pharmaceutical compositions) for administering a drug will depend on the mode of administration. For example, formulations adapted for parenteral administration may comprise a sterile aqueous preparation, preferably isotonic with the blood of the recipient. This aqueous preparation may be formulated according to known methods using suitable dispersing or wetting agents and suspending agents. Illustrative of a preparation produced in such conventional fashion is the aqueous formulation, Remestyp (terlipressin). The preparation also may be a sterile injectable solution or suspension in a diluent or solvent, for example as a solution in 1,3-butanediol, water, Ringer's solution, and isotonic sodium chloride solution, which are exemplary acceptable diluents. Sterile, fixed oils may be employed as a solvent or suspending medium. Bland fixed oils, including synthetic mono or di-glycerides, and fatty acids, such as oleic acid, may also be used. Most of the agents described herein are commercially available and can be obtained readily from commercial sources.

Excipients

The pharmaceutical compositions of the present invention may also contain diluents, fillers, salts, buffers, stabilizers, solubilizers, and other materials well known in the art. The term "pharmaceutically acceptable carrier" refers to a non-toxic carrier that may be administered to a patient, together with a therapeutically effective substance (such as angiotensin II) of this invention, and which does not destroy the pharmacological activity of the therapeutically effective substance. The term "pharmaceutically acceptable" means a non-toxic material that does not interfere with the effectiveness of the biological activity of the active ingredient(s). The characteristics of the carrier will depend on the route of administration. The term "excipient" refers to an additive in a formulation or composition that is not a pharmaceutically active ingredient.

One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to empirically determine which excipients, if any, to include in the compositions of the invention. Excipients of the invention may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some aspects, it may be beneficial to include a pharmaceutically acceptable carrier in the compositions of the invention.

Solubilizing Agents

In some aspects, it may be beneficial to include a solubilizing agent in the compositions of the invention. Solubilizing agents may be useful for increasing the solubility of any of the components of the formulation or composition, including a therapeutically effective substance (e.g., angiotensin II) or an excipient. The solubilizing agents described herein are not intended to constitute an exhaustive list, but are provided merely as exemplary solubilizing agents that may be used in the compositions of the invention. In certain aspects, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

pH-Adjusting Agents

In some aspects, it may be beneficial to adjust the pH of the compositions by including a pH-adjusting agent in the compositions of the invention. Modifying the pH of a formulation or composition may have beneficial effects on, for example, the stability or solubility of a therapeutically effective substance, or may be useful in making a formulation or composition suitable for parenteral administration. pH-adjusting agents are well known in the art. Accordingly, the pH-adjusting agents described herein are not intended to constitute an exhaustive list, but are provided merely as exemplary pH-adjusting agents that may be used in the compositions of the invention. pH-adjusting agents may include, for example, acids and bases. In some aspects, a pH-adjusting agent includes, but is not limited to, acetic acid, hydrochloric acid, phosphoric acid, sodium hydroxide, sodium carbonate, and combinations thereof.

The pH of the compositions of the invention may be any pH that provides desirable properties for the formulation or composition. Desirable properties may include, for example, therapeutically effective substance (e.g., angiotensin II) stability, increased therapeutically effective substance retention as compared to compositions at other pHs, and improved filtration efficiency. In some aspects, the pH of the compositions of the invention may be from about 3.0 to about 9.0, e.g., from about 5.0 to about 7.0. In particular aspects, the pH of the compositions of the invention may be 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, or 6.5±0.1.

Buffers

In some aspects, it may be beneficial to buffer the pH by including one or more buffers in the compositions. In certain aspects, a buffer may have a pKa of, for example, about 5.5, about 6.0, or about 6.5. One of skill in the art would appreciate that an appropriate buffer may be chosen for inclusion in compositions of the invention based on its pKa and other properties. Buffers are well known in the art. Accordingly, the buffers described herein are not intended to constitute an exhaustive list, but are provided merely as exemplary buffers that may be used in the compositions of the invention. In certain aspects, a buffer may include one or more of the following: Tris, Tris HCl, potassium phosphate, sodium phosphate, sodium citrate, sodium ascorbate, combinations of sodium and potassium phosphate, Tris/Tris HCl, sodium bicarbonate, arginine phosphate, arginine hydrochloride, histidine hydrochloride, cacodylate, succinate, 2-(N-morpholino)ethanesulfonic acid (MES), maleate, bistris, phosphate, carbonate, and any pharmaceutically acceptable salts and/or combinations thereof Surfactants In some aspects, it may be beneficial to include a surfactant in the compositions of the invention. Surfactants, in general, decrease the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the compositions of the invention. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof Tonicity-Adjusting Agents In some aspects, it may be beneficial to include a tonicity-adjusting agent in the compositions of the invention. The tonicity of a liquid composition is an important consideration when administering the composition to a patient, for example, by parenteral administration. Tonicity-adjusting agents, thus, may be used to help make a formulation or composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the compositions of the invention. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

Stabilizing Agents

In some aspects, it may be beneficial to include a stabilizing agent in the compositions of the invention. Stabilizing agents help increase the stability of a therapeutically effective substance in compositions of the invention. This may occur by, for example, reducing degradation or preventing aggregation of a therapeutically effective substance. Without wishing to be bound by theory, mechanisms for enhancing stability may include sequestration of the therapeutically effective substance from a solvent or inhibiting free radical oxidation of the anthracycline compound. Stabilizing agents are well known in the art. Accordingly, the stabilizing agents described herein are not intended to constitute an exhaustive list, but are provided merely as exemplary stabilizing agents that may be used in the compositions of the invention. Stabilizing agents may include, but are not limited to, emulsifiers and surfactants.

Modes of Administration

Administration of angiotensin II or a catecholamine can be by any convenient route, e.g. intravenous (using either a bolus or by a steady infusion), intramuscular, subcutaneous or inhalation. The angiotensin II and the catecholamine may be administered together or independently.

The compositions of the invention can be administered in a variety of conventional ways. In some aspects, the compositions of the invention are suitable for parenteral administration. These compositions may be administered, for example, intraperitoneally, intravenously, intrarenally, or intrathecally. In some aspects, the compositions of the invention are injected intravenously. One of skill in the art would appreciate that a method of administering a therapeutically effective substance formulation or composition of the invention would depend on factors such as the age, weight, and physical condition of the patient being treated, and the disease or condition being treated. The skilled worker would, thus, be able to select a method of administration optimal for a patient on a case-by-case basis.

Unless otherwise defined herein, scientific and technical terms used in this application shall have the meanings that are commonly understood by those of ordinary skill in the art. Generally, nomenclature and techniques relating to chemistry, molecular biology, cell and cancer biology, immunology, microbiology, pharmacology, and protein and nucleic acid chemistry, described herein, are those well-known and commonly used in the art.

Methods Related to the Administration of Angiotensin II

One aspect of the invention is a method comprising administering to a subject having high output shock (e.g., catecholamine-resistant high output shock) and undergoing treatment with a catecholamine at a dose equivalent to at least about 0.2 mcg/kg/min of norepinephrine a dose of angiotensin II which is effective to raise the blood pressure of the subject to a mean arterial pressure (MAP) of about 65 mm Hg or above, and which is effective to reduce the dose of the catecholamine required to maintain a MAP of about 65 mm Hg to the equivalent of about 0.05-0.2 mcg/kg/min norepinephrine or less.

Another aspect of the invention is a method comprising administering to a subject having high output shock (e.g., catecholamine-resistant high output shock) and undergoing treatment with a catecholamine at a dose equivalent to at least about 5 mcg/min of norepinephrine a dose of angiotensin II which is effective to raise the blood pressure of the subject to a mean arterial pressure (MAP) above about 80 mm Hg, and which is effective to reduce the dose of the catecholamine required to maintain a MAP above about 80 mm Hg to the equivalent of less than about 5-10 mcg/min norepinephrine. In certain such embodiments, the dose of angiotensin H is at least about 20 ng/kg/min.

In various embodiments, the dose of angiotensin II is effective to reduce the dose of the catecholamine required to maintain a MAP of about 65 mm Hg to the equivalent of about 0.05 mcg/kg/min norepinephrine or less.

In embodiments of the invention,
a. the catecholamine is norepinephrine, or
b. the catecholamine is epinephrine and the dose equivalent to 0.1 mcg/kg/min of norepinephrine is 0.1 mcg/kg/min; or
c. the catecholamine is dopamine and the dose equivalent to 0.1 mcg/kg/min of norepinephrine is 15 mcg/kg/min; or d. the catecholamine is phenylephrine and the dose equivalent to 0.1 mcg/kg/min of norepinephrine is 1.0 mcg/kg/min.

In embodiments of the invention, the dose of angiotensin II is from about 0.25 ng/kg/min to about 10 ng/kg/min, from about 0.25 ng/kg/min to about 5 ng/kg/min; about 1 ng/kg/min; about 2 ng/kg/min or about 3 ng/kg/min.

Another aspect of the invention is a method comprising administering to a subject having high output shock (e.g., catecholamine-resistant high output shock) and undergoing treatment with a catecholamine at a dose equivalent to at least about 0.2 mcg/kg/min of norepinephrine a dose of angiotensin II which is effective to raise the blood pressure of the subject to a MAP of about 65 mm Hg or above, and which is effective to reduce the dose of the catecholamine required to maintain a MAP of about 0.05 mcg/kg/min norepinephrine or less, which further comprises identifying the subject (selecting a subject) as belonging to the subset of subjects who are sufficiently responsive to angiotensin II so that a dose of angiotensin II of about 0.25 ng/kg/min to about 5 ng/kg/min is effective to reduce the amount of norepinephrine required to maintain a mean arterial pressure (MAP) at or above about 65 mm Hg to about 0.05 mcg/kg/min epinephrine or less, by titrating the amount of angiotensin with regard to a fixed dose of norepinephrine; and continuing to administer angiotensin II to the subject, at the dose determined as above.

In various methods of the invention, the angiotensin II and the catecholamine may be administered intravenously, intramuscularly, subcutaneously or by inhalation; and they may be administered together or independently.

Another aspect of the invention is a method comprising administering to a subject having shock (e.g., septic shock or shock from other causes, such as cardiac arrest or cardiogenic shock) and undergoing treatment with a catecholamine at a dose equivalent to at least about 0.2 mcg/kg/min of norepinephrine a dose of angiotensin II which is effective to raise the blood pressure of the subject to a MAP of about 65 mm Hg or above, and which is effective to reduce the dose of the catecholamine required to maintain a MAP of about 65 mm Hg to the equivalent of about 0.05-0.2 mcg/kg/min norepinephrine or less, or to the equivalent of about 0.05 mcg/kg/min norepinephrine or less.

In some methods of the invention, the subject is a human.

In certain embodiments, the angiotensin II and the catecholamine are conjointly administered. As used herein, the phrase "conjoint administration" refers to any form of administration of two agents such that the second agent is administered while the previously administered agent is still effective in the body (e.g., the two agents are simultaneously effective in the patient, which may include synergistic effects of the two agents). For example, the two agents can be administered either in the same formulation or in separate formulations, either concomitantly or sequentially. In certain embodiments, the different agents can be administered within one hour, 12 hours, 24 hours, 36 hours, 48 hours, 72 hours, or a week of one another. Thus, an individual who receives such treatment can benefit from a combined effect of the two agents.

In various methods of the invention, the subject is undergoing standard-of-care treatment with a catecholamine (e.g., epinephrine, norepinephrine, dopamine, phenylephrine, ephedrine) or with vasopressin at or prior to the time the angiotensin II is administered. These agents are administered at a dose which is equivalent to at least 0.2 mcg/kg/min of the catecholamine, noreninenhrine. Typical equivalent doses are:

| Drug | Dose | Norepinephrine Equivalent |
| --- | --- | --- |
| Epinephrine | 0.1 mcg/kg/min | 0.1 mcg/kg/min |
| Norepinephrine | 0.1 mcg/kg/min | 0.1 mcg/kg/min |
| Dopamine | 15 mcg/kg/min | 0.1 mcg/kg/min |
| Phenylephrine | 1.0 mcg/kg/min | 0.1 mcg/kg/min |
| Vasopressin | 0.04 U/min | 0.1 mcg/kg/min |

In some embodiments, the patients are catecholamine-resistant. That is, the patients are not responsive (do not exhibit an increase in blood pressure) to a catecholamine administered in a dose that is equivalent to a dose of at least about 0.2 mcg/kg/min of norepinephrine.

One skilled in the art will readily appreciate that the present invention is well adapted to carry out the objects and obtain the ends and advantages mentioned, as well as those inherent therein. The embodiments described herein are not intended as limitations on the scope of the invention. The present description is further illustrated by the following examples, which should not be construed as limiting in any way. In the foregoing and in the following examples, all temperatures are set forth in uncorrected degrees Celsius; and, unless otherwise indicated, all parts and percentages are by weight.

EXAMPLES

Example I—Intravenous Angiotensin II for the Treatment of High Output Shock

A. Methods

Study Patients

Patients were older than 21 years of age and deemed to have high output shock, defined as a cardiovascular Sequential Organ Function Assessment (SOFA) score of 4 as well as a cardiac index of >2.4 liters/min/BSA 1.73 m² [10]. Patients also had an indwelling arterial line and urinary catheter as part of standard care. In addition, each subject was found to be adequately volume resuscitated and clinically assessed not to be volume responsive (i.e. a fluid bolus would fail to increase cardiac index by 15%). Standard of care was to resuscitate with 20-30 cc/kg of crystalloid as initial resuscitation. Exclusion criteria included patients with acute coronary syndrome, a known history of vasospasm or asthma, any patients currently experiencing bronchospasm or patients with active bleeding with an anticipated need for transfusion of >4 units of packed red blood cells, hemoglobin<7 g/dL or any other condition that would contraindicate drawing serial blood samples.

Treatment Assignments

Upon enrollment in the study, patients were randomly assigned the following randomization procedures (computerized random numbers) to receive either angiotensin II acetate infusion (Clinalfa, Bachem AG, Hauptstrasse 144, 4416 Bubendorf, Switzerland) or a placebo infusion (hereafter referred to as the Study Drug and placebo, respectively). The investigators, clinical support staff, the patients and their families were unaware of the treatment assignment for the duration of the study.

Drug Infusion

Enrolled patients were randomized to receive the Study Drug infusion in normal saline calculated to run at a drip rate corresponding to an initial concentration of 20 ng/kg/min, plus the standard-of-care treatment for high output shock. The Study Drug was prepared in an opaque cellophane bag, the contents of which were unknown to the investigators, nurses or anyone else taking direct care of the patient. The Study Drug was administered for a total of 6 hours, with dose (and corresponding drip rate) adjustments made hourly. Study Drug dose adjustments were determined per a pre-specified protocol, based on the concomitant requirements of standard-of-care therapy (in all cases, norepinephrine infusion plus vasopressin, epinephrine and/or phenylephrine infusions) needed to maintain a mean arterial pressure (MAP) at or above 65 mm Hg, which is the standard practice at our institution. The Study Drug titration protocol was designed to elucidate the dose of ATII that was required (in conjunction with a norepinephrine dose between 5-10 mcg/min) to achieve the aforementioned standard MAP goal of 65 mm Hg. The dose titration protocol is shown on FIG. 1. The maximum allowable dose for the ATII titration was 40 ng/kg/min, and the minimum was 5 ng/kg/min. At the end of 6 hours, the Study Drug infusion was titrated off by being halved every 10 minutes until the Study Drug infusion dose was below 5 ng/kg/min, after which it was discontinued.

End Points

The primary endpoint was the effect of the ATII infusion on the standing dose of norepinephrine which was required to maintain a MAP of 65 mmHg. The secondary endpoints included the effect of the ATII infusion on urine output, serum lactate, cardiac output, and 30 day mortality.

Statistical Analysis

A small cohort of patients was analyzed, consistent with similar studies of this nature. A population of 20 patients, ten patients in each arm, was determined to generate a basis for determining if ATII could affect the dose of norepinephrine at the doses outlined herein. An independent data and safety monitor (DSM) was assigned and reviewed all adverse events.

The distribution of demographic and clinical variables was also assessed. Differences between proportions of patients with certain variables were assessed with the chi-square, Fisher exact test, student t, and Mann-Whitney test as appropriate. The primary endpoint of the effect of the Study Drug infusion on the standing dose of norepinephrine was calculated using a general estimating equation analysis and is presented as the mean dose of norepinephrine (mcg/min) and Study Drug infusion (in ng/kg/min) at hourly intervals.

Generalized estimating equation was used to model the response to the Study Drug over time, with standard-of-care vasopressor hourly readings beginning at 1 hour prior to, through 8 hours after the initiation of the Study Drug, using the SAS Genmod procedure (version 9.3, Cary, N.C.). Correlation structure was defined as auto-regressive to account for the likely higher correlation between time points that were closer together. In this model, the main effect of drug examines the mean response to each drug averaged across times. The main effect of time examines the mean response at each time point averaged across drugs, and the drug multiplied by time interaction examines whether the change over time differs between drugs.

All values are reported as mean±standard deviation unless otherwise specified. All other statistical analysis was completed using SPSS 18, Chicago, Ill., USA.

B. Results

Figure 2:
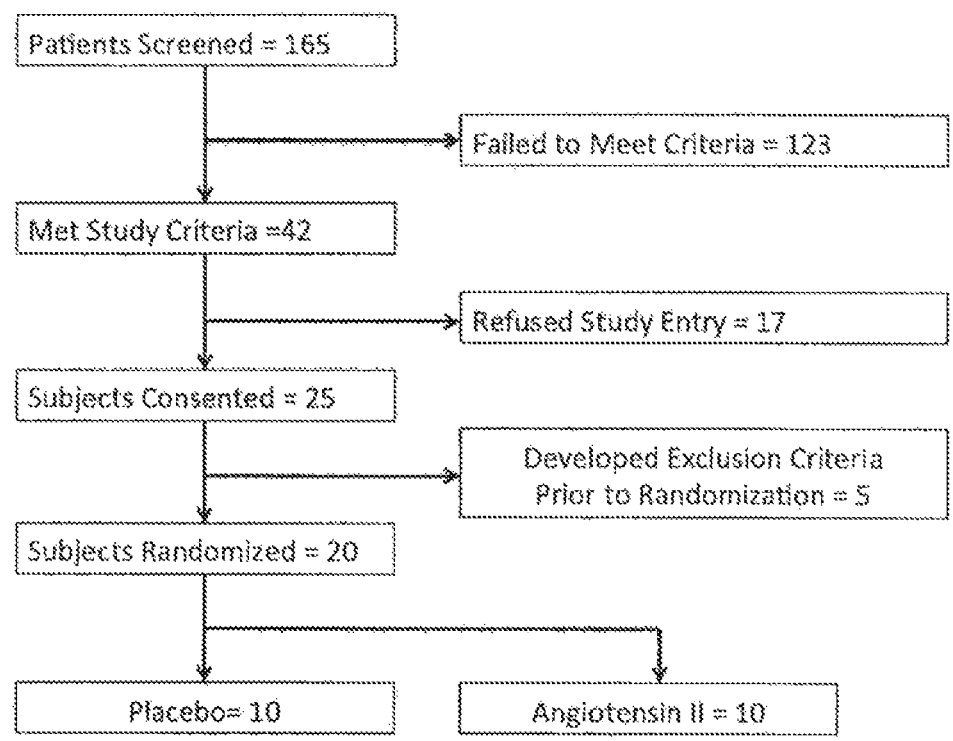
FIG. 2 shows patient flow diagram.
Figure 3:
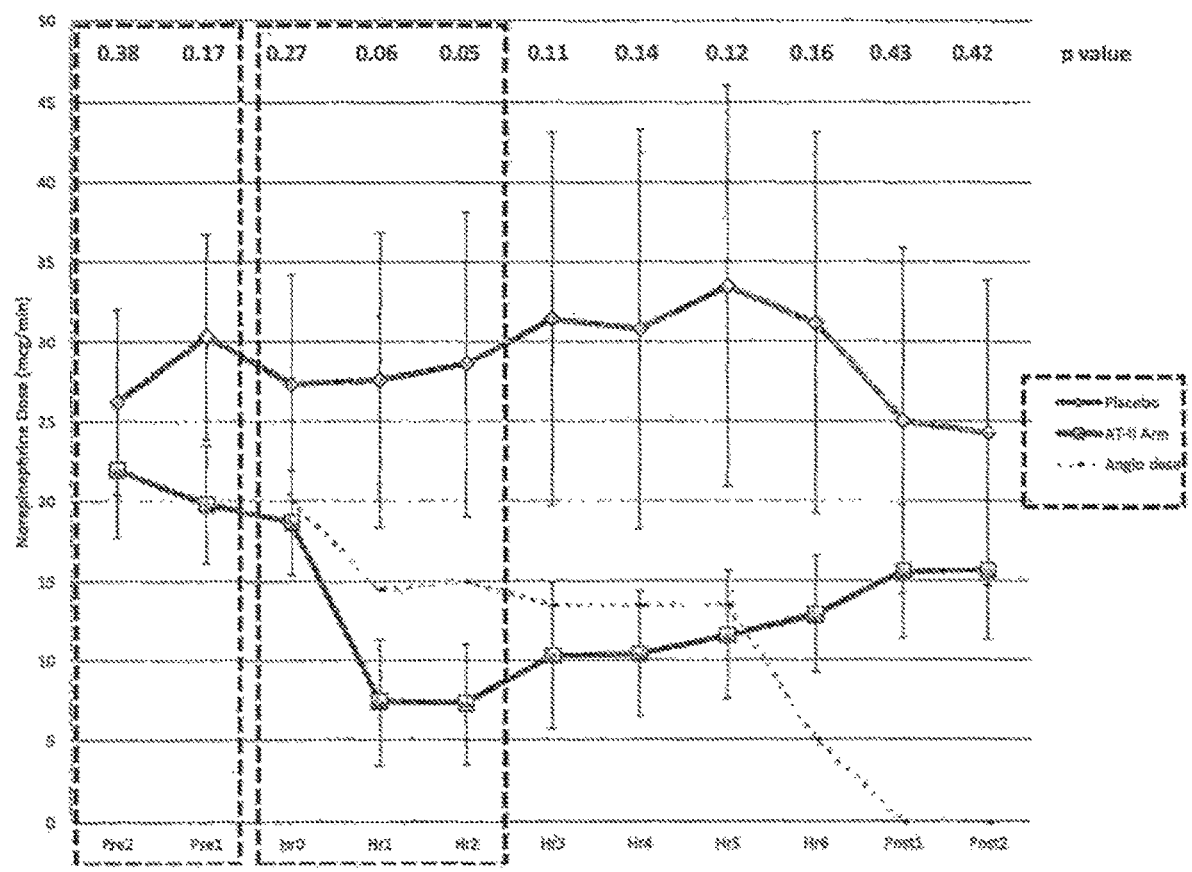
FIG. 3 shows changes in norepinephrine dose with concurrent angiotensin II.

The flow of patients into the study is reported in FIG. 2. Twenty patients underwent randomization and all 20 patients were enrolled in and completed the study (FIG. 1). Baseline characteristics of the two groups are shown in Table 1. The mean age for all study subjects was 62.9±15.8 years. Of the patients, 75% were male, 45% were Caucasian and 40% were African American. Baseline SOFA and APACHE II scores were 15.9±3.0 and 30.6±8.9, respectively. 19 of 20 patients were receiving concomitant vasopressin at a dose of 0.02-0.08 u/min. Vasopressin doses were not adjusted during the study period ATII resulted in a reduction in norepinephrine dosing in all patients (FIG. 3). The mean Hour 1 norepinephrine dose for the placebo cohort was 27.6±29.3 mcg/min v. 7.4±12.4 mcg/min for the ATII cohort (p=0.06). Hour 2 norepinephrine dosing for the placebo cohort was 28.6±30.2 mcg/min v. 7.3±11.9 mcg/min in the ATII cohort (p=0.06). Throughout the study period, the mean ATII dose was reduced from 20 ng/kg/min at Hour Zero to 5 ng/kg/min at Hour 6 before being titrated off by Hour 7 (one hour post-infusion). Despite this down-titration of ATII, norepinephrine doses remained substantially lower in the ATII cohort than the placebo cohort, though the effect approached statistical significance only at Hours 1 and 2. Upon cessation of the ATII infusion, mean norepinephrine rebounded concomitantly.

Using a general estimating equation model with time defined as a continuous variable, in order to obtain a global test of interaction effect, the main effect of treatment (Study Drug vs. placebo) was not significant (p=0.13), nor was the effect of time (p=0.30), nor was the treatment multiplied by time interaction (p=0.76). When time was defined as a class variable with Hour −1 defined as the reference group, in order to examine specific time points, the drug effect (p=0.14) and time effect (p=0.18 at time 0, p=0.51 at time 1) both remained non-significant. The product of drug multiplied by time interaction showed a trend level of significance at 1-hr and 2-hr (p=0.06).

Adverse events most commonly experienced by all patients were metabolic disorders with alkalosis occurring in four patients in the ATII group and zero in the placebo group (p=0.09). The most common adverse event thought to be attributable to ATII was hypertension, which occurred in 20% of patients receiving ATII (p=0.58). In both of these patients, the Study Drug infusion was stopped, per protocol, in order to achieve MAP goals. Table 2 lists adverse events Urine output, cardiac output, central venous pressure, and mean arterial pressure are shown in Table 3. The 30 day mortality for the two groups were similar for the ATII cohort and the placebo cohort (50% v. 60%, p=1.00).

TABLE 1

| Baseline demographic and clinical data | | | | | | | |
|---|---|---|---|---|---|---|---|
| | Full Cohort | SD | ATII | SD | Placebo | SD | P value[1] |
| Age | 62.85 | 15.81 | 68.40 | 17.46 | 57.30 | 12.44 | 0.12 |
| Male (n) | 15 | | 6 | | 9 | | 0.30 |
| Race (n) | | | | | | | |
| Caucasian | 9 | | 6 | | 3 | | 0.37 |
| Black | 8 | | 3 | | 5 | | 0.65 |
| Other | 3 | | 1 | | 2 | | 1.00 |

TABLE 1-continued

Baseline demographic and clinical data

| | Full Cohort | SD | ATII | SD | Placebo | SD | P value[1] |
|---|---|---|---|---|---|---|---|
| Severity of Illness | | | | | | | |
| Baseline SOFA | 15.90 | 2.97 | 14.9 | 2.81 | 16.90 | 2.92 | 0.14 |
| APACHE | 30.60 | 8.86 | 27.2 | 9.67 | 34.00 | 6.83 | 0.09 |
| Past Medical History | | | | | | | |
| IHD | 2 | | 1 | | 1 | | 1.00 |
| CHF | 2 | | 2 | | 0 | | 0.47 |
| COPD | 2 | | 2 | | 0 | | 0.47 |
| DM | 7 | | 4 | | 3 | | 1.00 |
| CKD | 7 | | 3 | | 4 | | 1.00 |
| HD | 1 | | 0 | | 1 | | 1.00 |
| Liver disease | 9 | | 5 | | 4 | | 1.00 |
| Cancer | 6 | | 1 | | 5 | | 0.14 |
| IS | 6 | | 1 | | 5 | | 0.14 |
| Steroids | 3 | | 1 | | 2 | | 1.00 |
| Hypertension | 9 | | 4 | | 5 | | 1.00 |
| CVA | 5 | | 4 | | 1 | | 0.30 |
| AKI | 17 | | 9 | | 8 | | 1.00 |
| Labs | | | | | | | |
| WBC | 17.38 | | 19.0 | 16.0 | 15.72 | 12.3 | 0.61 |
| Hgb | 9.45 | | 9.16 | 2.14 | 9.73 | 2.45 | 0.59 |
| Creatinine | 2.33 | | 1.89 | 1.03 | 2.76 | 1.34 | 0.12 |
| pH | 7.33 | | 7.34 | 0.11 | 7.32 | 0.12 | 0.63 |
| Lactate | 5.83 | | 4.59 | 3.11 | 7.06 | 5.16 | 0.21 |
| Baseline vasopressor doses[Y] | | | | | | | |
| Norepinephrine | 25.05 | 17.03 | 19.80 | 11.67 | 30.30 | 20.37 | 0.18 |
| Vasopressin | 0.04 | 0.02 | 0.03 | 0.02 | 0.05 | 0.02 | 0.10 |

Results are presented as mean and SD or number.
[1] P values for continuous variables calculated using Student's T test. P values for discrete variables calculated using Fisher exact test.
[2] One patient in the placebo group received phenylephrine infusion prior to initiation of ATII versus no patients in the ATII group. One patient in the placebo group received epinephrine versus no patients in the ATII group.
SOFA, sequential organ function assessment;
APACHE, acute physiology an chronic health evaluation II;
IHD = ischemic heart disease.
CHF = congestive heart failure.
COPD = chronic obstructive pulmonary disease.
DM = diabetes mellitus.
CKD = chronic kidney disease.
HD = hemodialysis.
IS = immunocompromised state.
CVA = cerebrovascular accident.
AKI = acute kidney injury; Hgb, hemoglobin;
NA, to represent not analyzed, not applicable, or not available.

TABLE 2

Adverse events

| Organ System | Total | ATII | Placebo | P value |
|---|---|---|---|---|
| Metabolic disorders | 16 | 11 | 5 | |
| Acidosis | | 2 | 3 | 1.00 |
| Alkalosis | | 4 | 0 | 0.09 |
| Blood or lymphatic disorders | 7 | 3 | 4 | |
| Respiratory disorders | 6 | 3 | 3 | |
| Worsening respiratory failure | | 1 | 3 | 0.58 |
| Wheezing | | 1 | 0 | 1.00 |
| Cardiac disorders | 12 | 7 | 5 | |
| Hypertension[◊] | | 2 | 0 | 0.58 |
| Hypotension | | 2 | 1 | 1.00 |
| Atrial Fibrillation | | 2 | 0 | 0.47 |
| Renal disorders[γ] | 7 | 6 | 1 | |
| Decreased urine output | | 3 | 1 | 0.58 |
| Worsening AKI | | 0 | 2 | 0.47 |
| Other disorders[†] | 8 | 5 | 3 | |
| Worsening MOSF | | 2 | 3 | 1.00 |

[◊] ATII infusion was discontinued in two patients due to hypertension.
[γ] Seventeen of 20 patients exhibited pre-existing AKI, including 8 patients receiving placebo and 9 patients receiving ATII. Of the three patients that did not have pre-existing AKI, one patient developed AKI and received ATII.
[†] Includes worsening multiple organ system failure, fever, lower extremity edema, and thigh hematoma.
AKI = acute kidney injury.
MOSF = multiple organ system failure.
P values calculated using Fisher Exact test.

Urine output, cardiac output, central venous pressure, and mean arterial pressure are shown in Table 3. The 30 day mortality for the two groups were similar for the ATII cohort and the placebo cohort (50% v. 60%, p=1.00).

TABLE 3

| Secondary outcomes | | | | | | | | | | | |
|---|---|---|---|---|---|---|---|---|---|---|---|
| | Hr-2 | Hr-1 | Hr 0 | Hr 1 | Hr 2 | Hr 3 | Hr 4 | Hr 5 | Hr 6 | Hr 7 | Hr 8 |
| Urine Output | | | | | | | | | | | |
| ATII | 41.7(51.7) | 28.6(32.4) | 45.9(96.5) | 31.1(58.0) | 33.7(67.1) | 42.6(59.8) | 35.9(50.0) | 34.4(57.2) | 36.1(38.3) | 27.2(33.3) | 23.8(27.3) |
| Placebo | 29.5(69.8) | 12.4(23.2) | 23.5(41.8) | 17.5(25.7) | 17.0(32.0) | 16.3(24.6) | 17.0(34.7) | 16.8(30.4) | 14.8(26.3) | 18.0(27.3) | 23.0(34.4) |
| Cardiac Output | | | | | | | | | | | |
| ATII | 2.0(2.7) | 6.0(3.1) | 6.6(2.6) | 6.3(2.5) | 6.2(2.5) | 5.9(2.7) | 6.5(2.4) | 6.1(2.6) | 6.7(3.3) | 6.3(2.9) | 7.5(3.1) |
| Placebo | 6.3(1.2) | 6.9(2.5) | 6.5(1.7) | 6.9(1.8) | 6.4(1.7) | 6.8(3.0) | 2.3(2.2) | 6.8(1.5) | 7.3(1.8) | 6.9(2.5) | 7.0(2.3) |
| CVP | | | | | | | | | | | |
| ATII | 12.2(5.5) | 12.9(7.0) | 14.1(8.9) | 14.8(7.3) | 14.6(7.4) | 14.8(8.8) | 11.7(3.9) | 12.1(4.8) | 10.0(2.9) | 12.6(4.8) | 11.8(3.8) |
| Placebo | 16.0(3.0) | 9.7(2.1) | 12.6(7.8) | 15.7(9.3) | 17.3(9.0) | 15.7(7.3) | 16.4(8.6) | 16.3(6.7) | 14.2(6.5) | 14.4(2.1) | 13.2(5.6) |
| MAP | | | | | | | | | | | |
| ATII | 71.2(13.6) | 72.3(11.2) | 68.8(7.0) | 74.8(8.4) | 69.8(8.6) | 73.1(12.5) | 75.3(14.2) | 68.9(8.1) | 73.0(10.5) | 72.3(11.9) | 73.6(11.5) |
| Placebo | 71.2(9.2) | 71.8(6.3) | 73.0(12.6) | 72.8(9.3) | 67.8(6.6) | 70.1(6.4) | 71.3(7.8) | 73.0(4.7) | 75.9(9.4) | 74.0(10.6) | 74.5(13.2) |
| Lactate | | | | | | | | | | | |
| ATII | | | 4.6(3.1) | | | | | | 5.2(4.1) | | |
| Placebo | | | 7.1(5.2) | | | | | | 5.7(3.9) | | |

Legend:
Urine Output (cc).
Cardiac Output (liters/min),
CVP = central venous pressure;
all variables-mean (s.d.),
* denotes p < 0.05.

Further studies showed that subjects who are administered as little as 1.25 or 2.5 ng/kg/min of angiotensin II show an increase in blood pressure and maintain it, even in the absence of, or with very low doses of, a catecholamine, such as norepinephrine. The standard of care for patients with high-output shock is to maintain the mean arterial pressure at 65 mm of Hg with catecholamines and/or vasopressin. The inability to maintain blood pressure in mammals for an extended period of time is uniformly fatal. In the study illustrated in FIG. 4, the standard of care was to administer norepinephrine. 20% of the patients responded to very low doses of angiotensin II (1.25-2.5 ng/kg/min) such that the MAP rose markedly. Per standard protocol, the catecholamine dose was decreased as pushing the MAP above normal in high-output shock patients is non-standard. Even as the catecholamines were completely weaned off, the low dose of Angiotensin II resulted in a MAP>85 mm of Hg.

ATII was shown to be an effective pressor agent at a dose range of 1-40 ng/kg/min. More specifically, a starting dose of 2-10 ng/kg/min may be an appropriate starting dose in the treatment of high output shock when used in conjunction with standard-of-care vasopressors.

While all patients in the study had a response to the ATII infusion, significant heterogeneity was observed. Of the ten patients who received ATII, two had a modest response, while two were exquisitely sensitive to ATII, which was an unexpected finding. In the two highly sensitive patients, the norepinephrine infusion was titrated off per protocol, and the ATII dose was at its lowest allowable dose of 5 ng/kg/min and the patients remained hypertensive with MAP of >90 mm Hg despite norepinephrine titrated off. Since hypertension is not part of our standard of care, the investigators halted the infusion, and the ATII was weaned off. In both cases the need for norepinephrine was rapidly reestablished.

ATII appears to have synergy with other vasopressors (i.e. catecholamines and vasopressin). It appears that for patients who require norepinephrine and are tachycardic, ATII is particularly useful. For patients with severe hypotension, lower doses of multiple vasopressors with differing mechanisms of action may be more efficacious and less toxic than high doses of one type of vasopressors (i.e., catecholamines).

Among the multiple strengths of the present study are the following. First, the study was a randomized, double-blind controlled trial with an appropriate placebo control arm. Secondly, it was of pragmatic design, as it was the intent of the investigators to enroll patients receiving standard-of-care treatment for high output shock. As such, all patients had received a priori appropriate monitoring and therapeutic interventions (including central venous lines, bladder catheters, arterial lines, and cardiac output monitoring devices). There was no additional need for any specialized equipment of procedures prior to enrollment in the study. Thirdly, all enrolled patients had a documented need for high dose vasopressor therapy despite volume therapy, as evidenced by the cardiac index entry criteria. This is in keeping with the current practice of addressing volume responsiveness in a hypotensive patient prior to initiation of vasopressor therapy. Finally, as part of the study protocol, a data safety monitor was employed, who had the ability to unblind data and evaluate for adverse events as well as halt the study, neither of which occurred.

The initiation of an ATII infusion in patients receiving norepinephrine for septic shock resulted in a marked decrease in norepinephrine doses. ATII improved blood pressure in patients with high-output shock and multiple vasopressors. ATII is an effective as a pressor agent in the treatment of high output shock. Initial dosing can range from between 2-10 ng/kg/min. Finally, ATII was shown to be well-tolerated.

Another aspect of the present invention relates, inter alia, to formulations (compositions, pharmaceutical compositions) comprising angiotensin II in combination with one or more further peptides and/or compounds, as well as methods for the use of those formulations in the treatment of subjects in need of increased blood pressure (having hypotension), e.g. as present in a variety of types of shock, such as, e.g., high output shock, septic shock or shock from other forms of shock such as cardiac arrest or cardiogenic shock. The formulations can also be used to treat other conditions, including i.a. acute kidney injury, hepato-renal syndrome (HRS) or variceal bleeding.

Particular embodiments include, e.g., angiotensin II in combination with other vasopressor peptides or analogues or derivatives thereof; and angiotensin II in combination with other vasopressor peptides or analogs or derivatives thereof and a catecholamine. Additional embodiments include any of the preceding peptides or combinations further in combination with the compound methylene blue, also referred to herein as 3,7-bis(dimethylamino)-phenothiazin-5-ium chloride or MB.

The present inventor has found, unexpectedly, that the use of angiotensin II in combination with other vasopressors, such as vasopressin and/or vasopressin analogues and/or with catecholamines allows for the use of much lower doses of the vasopressin and/or vasopressin analogues and/or catecholamine than are currently administered as the standard of care, thereby reducing side effects of those agents and increasing efficiency. Methylene blue, also, exhibits a synergistic effect with any of these agents. That is, a combination of low doses of two or more of these agents (in combination with angiotensin II) is more effective than conventional large doses of one of the agents.

One aspect of the invention is a composition comprising angiotensin II or an analogue thereof and at least one additional vasopressor and/or methylene blue. Such combinations are sometimes referred to herein as "multicomponent compositions of the invention."

In embodiments of the invention, the multicomponent composition comprises the following combinations of agents:
angiotensin II+vasopressin
angiotensin II+vasopressin+norepinephrine
angiotensin II+vasopressin+any catecholamine,
methylene Blue (MB)+angiotensin II
MB+angiotensin II+vasopressin
MB+angiotensin II+vasopressin+norepinephrine
MB+angiotensin II+vasopressin+any catecholamine
angiotensin II+terlipressin
angiotensin II+terlipressin+norepinephrine
angiotensin II+terlipressin+any catecholamine
methylene blue (MB)+angiotensin II
MB+angiotensin II+terlipresssin
MB+angiotensin II+terlipresssin+norepinephrine
MB+angiotensin II+terlipressin+any catecholamine Another aspect of the invention is a pharmaceutical composition comprising a multicomponent composition as above and a pharmaceutically acceptable carrier.

Another aspect of the invention is a kit comprising, in one or more containers, angiotensin II and at least one additional vasopressor and/or methylene blue.

Another aspect of the invention is a method (e.g. a method for treating a subject in need thereof, e.g. in need of increased blood pressure, such as shock), comprising administering to the subject a therapeutically effective amount of a multicomponent composition comprising angiotensin II and at least one additional vasopressor and/or methylene blue, or with a pharmaceutical composition comprising the composition and a pharmaceutically acceptable carrier.

As was discussed above, agents such as the agents noted above can be administered conjointly, which refers to any form of administration of two agents (or more) such that the second agent (or additional agent(s)) is administered while the previously administered agent is still effective in the body (e.g., the two (or more) agents are simultaneously effective in the patient). For example, two (or more) agents can be administered either in the same formulation or in separate formulations, either concomitantly or sequentially. In certain embodiments, the different agents can be administered within one hour, 12 hours, 24 hours, 36 hours, 48 hours, 72 hours, or a week of one another. Thus, an individual who receives such treatment can benefit from a combined effect of the two or more agents. Two, three or four of the agents indicated above can be administered conjointly.

A composition for administering combinations of two or more of the indicated agents can take any of a variety of forms. For example, two of more of the agents can be packaged together and administered together. In another embodiment, one or more of the agents in a composition is packaged separately from the others, so it can be administered independently from the others, e.g., in a separate I.V. line. In this manner, for example, doses of the individual agents can be controlled individually. In one embodiment, for example in an emergency when a patient has had a cardiac arrest, the subject can be administered a combination of, e.g., angiotensin II, vasopressin and a catecholamine outside of the hospital, such as in an ambulance. Later, after the patient has arrived at the hospital, more refined doses and combinations of agents can be administered.

Angiotensin II is discussed above. The dose of angiotensin II which is administered to a subject in the context of multicomponent administration can be determined (titrated when used in combination with a catecholamine, vasopressin and/or methylene blue) by a method as discussed elsewhere herein. Generally, the dose of angiotensin II administered to a subject in the context of multicomponent administration is from about 1 or 1.25 ng/kg to about 20 ng/kg, from about 1 or 1.25 ng/kg/min to about 10 ng/kg/min, from about 1 or 1.25 ng/kg/min to about 5 ng/kg/min, from about 0.25 ng/kg/min to about 20 ng/kg/min, from about 0.25 ng/kg/min to about 10 ng/kg/min, or from about 0.25 ng/kg/min to about 5 ng/kg/min. In embodiments of the invention, the dose is about 0.25 ng/kg/min, about 0.5 ng/kg/min, about 1 ng/kg/min, about 1.25 ng/kg/min, about 1.5 ng/kg/min, about 2 ng/kg/min, about 2.5 ng/kg/min, about 3 ng/kg/min, about 3.5 ng/kg/min, about 4 ng/kg/min, about 4.5 ng/kg/min, about 5 ng/kg/min, about 5.5 ng/kg/min, about 6 ng/kg/min, about 7.5 ng/kg/min or about 10 ng/kg/min.

As was discussed above, the catecholamines that can be used in a method of the invention include, i.a., norepinephrine, epinephrine, dopamine or phenylephrine or ephedrine. The dose of a catecholamine which is administered to a subject in the context of multicomponent administration can be determined (titrated when used in combination with angiotensin II, vasopressin and/or methylene blue) by a method as discussed elsewhere herein. Generally, the dose of a catecholamine which is administered to a subject in the context of multicomponent administration is equivalent to a dose of norepinephrine of from about 0.01 mg/kg/min to about 0.1 mcg/kg/min (e.g. about 0.01, 0.02, 0.03, 0.04, 0.05, 0.06, 0.07, 0.08, 0.09 or 0.1 mcg/kg/min). Equivalent doses of catecholamines are summarized above.

Vasopressin or any of a variety of suitable analogues or derivatives thereof can be used in a method of the present invention; suitable analogues or derivatives will be evident to a skilled worker. Among these suitable analogues or derivatives are: terlipressin, argipressin, desmopressin, felypressin, lypressin, and ornipressin. One suitable analogue, terlipression, is a synthetic triglycyl-lysine derivative of vasopressin, which is an inactive prodrug. It has pressor and antidiuretic effects. Following intravenous (IV) injection, lysine vasopressin is released following the enzymatic cleavage of 3 glycyl moieties. The dose of vasopressin or an analogue thereof which is administered to a subject in the context of multicomponent administration can be determined (titrated when used in combination with angiotensin II, a catecholamine and/or methylene blue) by a method as discussed elsewhere herein. Generally, the dose of vasopressin which is administered to a subject in the context of multicomponent administration is about 0.01 U/min to about 0.04 U/min (e.g. about 0.01, about 0.02, about 0.03 or about 0.04 U/min). Generally, the dose of terlipressin which is administered to a subject in the context of multicomponent administration is about 0.1 mg to about 1 mg, e.g. about 0.1, 0.3, 0.7 or 1 mg, for about 4-6 hours.

Methylene blue (MB) can also be administered to a subject in a multicomponent administration method of the invention. Methylene blue is a selective inhibitor of guanylate cyclase, a second messenger involved in nitric oxide-mediated vasodilation, and as such can enhance the action of vasopressors. As an experimental pharmaceutical drug, the International Nonproprietary Name (INN) of methylene blue is methylthioninium chloride. The dose of methylene blue which is administered to a subject in the context of multicomponent administration can be determined (titrated when used in combination with angiotensin II, a catecholamine, and/or methylene blue) by a method as discussed elsewhere herein. Generally, the dose of methylene blue which is administered to a subject in the context of multicomponent administration is about 0.01 to about 3 mg/kg every 2-8 hours.

Treatment with the low doses of two or more of these agents (including angiotensin II) as noted above is more effective than conventional large doses of one of the agents. For example, the standard of care for administering a catecholamine by itself is in the range of about 0.01 to about 0.3 mcg/kg/min, and the standard of care for administering vasopressin in in the range of about 0.01 to about 0.08 U/min. By combining two or more of these components, a reduction of at least about 20% to about 25% of any of these over the conventional standard of care, represents a significant advantage.

The present inventor shows herein that smaller doses of multiple vasoconstrictors work more efficiently than large doses of one vasopressor. Without wishing to be bound by any particular mechanism, it is suggested that this synergy is due, at least in part, to the observation that vasopressin and angiotensin II affect different vascular beds differentially than catecholamines, so by attacking different targets, the agents act synergistically. For example, vasopressin tends to cause more mesenteric vasoconstriction than catecholamines, so if a patient develops mesenteric ischemia, vasopressin/vasopressin analogues are usually stopped. In diseases like hepato-renal syndrome, the disease problem is mesenteric vasodilation, and vasopressin/vasopressin analogues are deployed to counteract that specific regional vasodilation.

One embodiment of the invention is a kit which comprises angiotensin II and one of more of the agents vasopressin or an analogue thereof (e.g. terlipressin), and/or a catecholamine, and/or methylene blue. The agents in the kit can be present in individual containers (e.g. vials), or two or more agents can be present together in a single container. In one embodiment, each container contains a unit dose of the agent. In other embodiments, multiple dose units are present in each container. The agents may be in liquid form or they may be in solid (e.g. powdered or lyophilized form), which can be reconstituted with saline or a comparable diluent solution before administration to a patient. For example, in one embodiment, the following agents are present in solid form in a single vial: about 0.25 mg to about 1 mg of the catecholamine epinephrine; about 10 U to about 40 U of vasopressin; and about 0.01 micrograms to about 100 micrograms of angiotensin II. These components are then suspended in a suitable volume of a diluent before use. Suitable diluents and suitable amounts of other combinations of agents will be evident to a skilled worker.

Kits of the invention may comprise instructions for performing a method, such as methods for reconstituting solid forms of agents or for diluting liquid forms. Other optional elements of a kit of the invention include suitable buffers or other diluents for reconstituting solid forms of, or for diluting liquid forms of, the agents; or packaging materials. The reagents of the kit may be in containers in which the reagents are stable, e.g., in lyophilized or powdered form or stabilized liquids.

A composition or pharmaceutical composition of the invention can be used to treat any of a variety of diseases or conditions. These include, e.g., shock, including septic shock, shock from cardia arrest or cardiogenic shock, or high output shock. Other indications include acute kidney injury, hepato-renal syndrome (HRS) and variceal bleeding.

Acute Kidney Injury

Patients with inflammation/sepsis can develop acute kidney injury (AKI) due in part to vasodilation of glomerular efferent arteriole which causes intra-glomerular hypotension and loss of GFR. The parenteral use of agents such as angiotensin II and vasopressin causes efferent arteriole vasoconstriction, thereby mitigating this effect.

Hepato-Renal Syndrome (HRS)

HRS is a disease wherein mesenteric vasodilation is so profound that blood flows preferentially to the gut and away from the kidney. HRS occurs typically in patients with liver cirrhosis. Angiotensin II alone or in combination with vasopressin and/or a catecholamine causes vasoconstriction and consequent improvement in renal function. In addition, patients with cirrhosis often have vasodilation due to increased nitric oxide levels, and thus can be treated with methyelene blue in conjunction with angiotensin II and a vasopressin (e.g. terlipressin) and/or a catecholamine.

Variceal Bleeding

Patients with portal hypertension, usually from cirrhosis, tend to bleed from their esophageal varices. It is desirable to deploy drugs which decrease portal pressures. Treatment with a composition of the invention results in reduced bleeding, so fewer transfusions or procedures to stop bleeding are required, and death from the condition is reduced.

REFERENCES

1. Vincent J L, De Backer D: Circulatory shock. *N Engl J Med* 2013, 369(18):1726-1734.
2. Myburgh J A, Higgins A, Jovanovska A, Lipman J, Ramakrishnan N, Santamaria J, CAT Study investigators: A comparison of epinephrine and norepinephrine in critically ill patients. *Intensive Care Med* 2008, 34(12):2226-2234.
3. Rona G: Catecholamine cardiotoxicity. *J Mol Cell Cardiol* 1985, 17(4):291-306.
4. Morelli A, Ertmer C, Westphal M, Rehberg S, Kampmeier T, Ligges S, Orecchioni A, D'Egidio A, D'Ippoliti F, Raffone C, Venditti M, Guarracino F, Girardis M, Tritapepe L, Pietropaoli P, Mebazaa A, Singer M: Effect of heart rate control with esmolol on hemodynamic and clinical outcomes in patients with septic shock: a randomized clinical trial. *JAMA* 2013, 310(16):1683-1691.
5. Russell J A, Walley K R, Singer J, Gordon A C, Hebert P C, Cooper D J, Holmes C L, Mehta S, Granton J T, Storms M M, Cook D J, Presneill J J, Ayers D, VASST Investigators: Vasopressin versus norepinephrine infusion in patients with septic shock. *N Engl J Med* 2008, 358(9): 877-887
6. Basso N, Terragno N A: History about the discovery of the renin-angiotensin system. *Hypertension* 2001, 38(6): 1246-1249.
7. Struthers A D, MacDonald T M: Review of aldosterone- and angiotensin II-induced target organ damage and prevention. *Cardiovasc Res* 2004, 61(4):663-670.
8. Jackson T, Corke C, Agar J: Enalapril overdose treated with angiotensin infusion. *Lancet* 1993, 341(8846):703.
9. Trilli L E, Johnson K A: Lisinopril overdose and management with intravenous angiotensin II. *Ann Pharmacother* 1994, 28(10):1165-1168.
10. Vincent J L, Moreno R, Takala J, Willatts S, De Mendonca A, Bruining H, Reinhart C K, Suter P M, Thijs L G: The SOFA (Sepsis-related Organ Failure Assessment) score to describe organ dysfunction/failure. On behalf of the Working Group on Sepsis-Related Problems of the European Society of Intensive Care Medicine. *Intensive Care Med* 1996, 22(7):707-710.
11. Newby D E, Lee M R, Gray A J, Boon N A: Enalapril overdose and the corrective effect of intravenous angiotensin II. *Br J Clin Pharmacol* 1995, 40(1):103-104.
12. Wray G M, Coakley J H: Severe septic shock unresponsive to noradrenaline. *Lancet* 1995, 346(8990): I 604.
13. Whiteley S M, Dade J P: Treatment of hypotension in septic shock. *Lancet* 1996, 347(9000:622.
14. Ryding J, Heslet L, Hartvig T, Jonsson V: Reversal of 'refractory septic shock' by infusion of amrinone and angiotensin II in an anthracycline-treated patient. *Chest* 1995, 107(1):201-203.
15. Thomas V L, Nielsen M S: Administration of angiotensin II in refractory septic shock. *Crit Care Med* 1991, 19(8):1084-1086.
16. Yunge M, Petros A: Angiotensin for septic shock unresponsive to noradrenaline. *Arch Dis Child* 2000, 82(5): 388-389.
17. Correa T D, Jeger V, Pereira A J, Takala J, Djafarzadeh S, Jakob S M: Angiotensin II in Septic Shock: Effects on Tissue Perfusion, Organ Function, and Mitochondrial Respiration in a Porcine Model of Fecal Peritonitis. *Crit Care Med* 2014. August;42(8): e550-9
18. Wan L, Langenberg C, Bellomo R, May C N: Angiotensin II in experimental hyperdynamic sepsis. *Crit Care* 2009, 13(6):R190.
19. Goldsmith S R, Hasking G J: Effect of a pressor infusion of angiotensin II on sympathetic activity and heart rate in normal humans. *Circ Res* 1991, 68(1):263-268.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding specific embodiments are to be construed as merely illustrative, and not limiting of the scope of the invention in any way whatsoever. Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention.

The entire disclosure of all applications, patents, and publications cited above, including US provisional applications U.S. Provisional Application No. 61/917,576, filed Dec. 18, 2013, and U.S. Provisional Application No. 61/955, 706, filed Mar. 19, 2014, including the figures, are hereby incorporated in their entirety by reference, particularly with regard to the disclosure for which they are referenced.

What is claimed is:

1. A method of treating a human subject having distributive shock, comprising administering human Angiotensin II to the human subject at an initial rate of about 20 ng/kg/min and titrating the rate down to a rate sufficient to achieve or maintain a mean arterial pressure of greater than or equal to about 65 mmHg, wherein the Angiotensin II is in the form of a salt.

2. The method of claim 1, wherein the rate is titrated down one or more times by about 1.25 ng/kg/min to about 15 ng/kg/min.

3. The method of claim 1, wherein the rate is titrated down to about 1.25 ng/kg/min to less than 20 ng/kg/min over one or more titrations.

4. The method of claim 1, wherein the Angiotensin II is administered to the human subject over a period of about 0.25 hours to about 120 hours.

5. The method of claim 1, wherein the Angiotensin II is administered to the human subject over a period of about 1 hour to about 7 hours.

6. The method of claim 1, wherein the Angiotensin II is in the form of an acetate salt.

7. The method of claim 1, wherein the Angiotensin II is administered in a parenteral composition comprising aqueous sodium chloride.

8. The method of claim 7, wherein the Angiotensin II is administered in a parenteral composition comprising sodium hydroxide.

9. The method of claim 8, wherein the Angiotensin II is administered in a parenteral composition comprising hydrochloric acid.

10. The method of claim 9, wherein the Angiotensin II is administered in a parenteral composition having a pH of from about 3.0 to about 9.0.

11. The method of claim 1, wherein the Angiotensin II is administered in a parenteral composition having a pH of about 5.5.

12. The method of claim 1, wherein the Angiotensin II is administered to the human subject at a rate sufficient to achieve a mean arterial pressure of greater than or equal to about 80 mmHg.

13. The method of claim 1, wherein the Angiotensin II is administered to the human subject at a rate sufficient to maintain a mean arterial pressure of greater than or equal to about 65 mmHg.

14. The method of claim 13, wherein the mean arterial pressure is maintained at greater than or equal to about 65 mmHg for up to about 6 hours.

15. The method of claim 13, wherein the mean arterial pressure is maintained at greater than or equal to about 65 mmHg for about 6 hours or more.

16. The method of claim 1, wherein the Angiotensin II is administered to the human subject at a rate sufficient to maintain a mean arterial pressure of greater than or equal to about 80 mmHg.

17. The method of claim 16, wherein the mean arterial pressure is maintained at greater than or equal to about 80 mmHg for up to about 6 hours.

18. The method of claim 16, wherein the mean arterial pressure is maintained at greater than or equal to about 80 mmHg for about 6 hours or more.

19. The method of claim 1, wherein the human subject is undergoing treatment with one or more vasopressors.

20. The method of claim 19, wherein the one or more vasopressors is selected from the group consisting of norepinephrine, vasopressin, phenylephrine, epinephrine, and dopamine.

21. The method of claim 19, wherein the one or more vasopressors is norepinephrine or vasopressin.

22. The method of claim 1, wherein the human angiotensin II is synthetic human angiotensin II.

23. The method of claim 1, wherein the human angiotensin II consists of the sequence of SEQ ID NO. 1.

24. A method of treating a human subject having septic shock, comprising administering human Angiotensin II to the human subject at an initial rate of about 20 ng/kg/min and titrating the rate down to a rate sufficient to achieve or maintain a mean arterial pressure of greater than or equal to about 65 mmHg, wherein the Angiotensin II is in the form of a salt.

25. The method of claim 24, wherein the human angiotensin II is synthetic human angiotensin II.

26. The method of claim 24, wherein the human angiotensin II consists of the sequence of SEQ ID NO. 1.

27. A method of treating a human subject having septic shock or distributive shock, comprising
  (a) administering synthetic human Angiotensin II (SEQ ID NO. 1) to the human subject at an initial rate of about 20 ng/kg/min; and
  (b) titrating the rate down to a rate sufficient to achieve or maintain a target mean arterial pressure of greater than or equal to about 65 mmHg;

wherein the Angiotensin II is in the form of an acetate salt, and wherein the Angiotensin II is administered in a parenteral composition comprising aqueous sodium chloride, sodium hydroxide, and hydrochloric acid, and wherein the parenteral composition has a pH of about 5.5.

* * * * *